United States Patent
Blix et al.

(10) Patent No.: US 9,987,070 B2
(45) Date of Patent: Jun. 5, 2018

(54) ABLATION SYSTEM, METHODS, AND CONTROLLERS

(71) Applicant: St. Jude Medical, Cardiology Division, Inc., St. Paul, MN (US)

(72) Inventors: John B. Blix, Maple Grove, MN (US); James C. Baker, Woodbury, MN (US); Kevin K. Ennett, Lino Lakes, MN (US); John Eric Hein, Neenah, WI (US); Joseph Allen Brotz, Oshkosh, WI (US); Joseph William Barnier, Menasha, WI (US); Raymond Victor Froehlich, Neenah, WI (US); Michael Olsen, Savage, MN (US); Sukanya Varadharajan, Maplewood, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 289 days.

(21) Appl. No.: 14/204,139

(22) Filed: Mar. 11, 2014

(65) Prior Publication Data
US 2014/0276765 A1    Sep. 18, 2014

Related U.S. Application Data

(60) Provisional application No. 61/788,012, filed on Mar. 15, 2013, provisional application No. 61/817,550, (Continued)

(51) Int. Cl.
*A61B 18/12* (2006.01)
*A61B 18/08* (2006.01)
(Continued)

(52) U.S. Cl.
CPC .......... *A61B 18/08* (2013.01); *A61B 18/1206* (2013.01); *A61B 18/1492* (2013.01);
(Continued)

(58) Field of Classification Search
CPC ...... A61B 18/1206; A61B 2018/00636; A61B 2018/00642; A61B 2018/00654;
(Continued)

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| WO | 97/45157 | 12/1997 |
| WO | 00/66020 | 11/2000 |

(Continued)

OTHER PUBLICATIONS

Dibona, Gerald F., Neural Control of the Kidney: Functionally Specific Renal Sympathetic Nerve Fibers, American Journal of Physiology, 2000, 279, R1517-R1524.
(Continued)

*Primary Examiner* — Michael Peffley
(74) *Attorney, Agent, or Firm* — Armstrong Teasdale LLP

(57) ABSTRACT

Multi-electrode ablation systems, methods, and controllers are described. In one example, a multi-electrode ablation system includes a power supply configured to be coupled to a plurality of electrodes and a controller coupled to the power supply. The controller is configured to determine a thermal gain of each electrode of the plurality of electrodes. For each electrode of the plurality of electrodes, the controller sets a power limit based at least in part on said
(Continued)

electrode's determined thermal gain. The power limit establishes a maximum power that may be dissipated through said electrode.

20 Claims, 21 Drawing Sheets

Related U.S. Application Data filed on Apr. 30, 2013, provisional application No. 61/817,561, filed on Apr. 30, 2013.

(51) Int. Cl.
  *A61B 18/14* (2006.01)
  *A61B 18/00* (2006.01)
  *A61B 18/10* (2006.01)

(52) U.S. Cl.
  CPC .......... *A61B 18/10* (2013.01); *A61B 18/1233* (2013.01); *A61B 2018/00434* (2013.01); *A61B 2018/00577* (2013.01); *A61B 2018/00642* (2013.01); *A61B 2018/00654* (2013.01); *A61B 2018/00666* (2013.01); *A61B 2018/00702* (2013.01); *A61B 2018/00714* (2013.01); *A61B 2018/00779* (2013.01); *A61B 2018/00797* (2013.01); *A61B 2018/00815* (2013.01); *A61B 2018/00821* (2013.01); *A61B 2018/00827* (2013.01); *A61B 2018/00892* (2013.01); *A61B 2018/00898* (2013.01); *A61B 2018/1467* (2013.01)

(58) Field of Classification Search
  CPC .......... A61B 2018/00696; A61B 2018/00702; A61B 2018/00773; A61B 2018/00791; A61B 2018/00797; A61B 2018/00803; A61B 2018/00809; A61B 2018/00815; A61B 2018/00821; A61B 2018/00577; A61B 2018/00672; A61B 2018/00714; A61B 2018/00779; A61B 2018/0666; A61B 2018/0196; A61B 18/12; A61B 18/08; A61B 18/10; A61B 2018/1467; A61B 2018/0016; A61B 2018/00708; A61B 2018/00904
  See application file for complete search history.

(56) References Cited

U.S. PATENT DOCUMENTS

| | | | |
|---|---|---|---|
| 5,035,694 A | 7/1991 | Kasprzyk et al. | |
| 5,255,679 A | 10/1993 | Imran | |
| 5,300,068 A | 4/1994 | Rosar et al. | |
| 5,368,591 A | 11/1994 | Lennox et al. | |
| 5,387,233 A | 2/1995 | Alferness et al. | |
| 5,465,717 A | 11/1995 | Imran et al. | |
| 5,531,779 A | 7/1996 | Dahl et al. | |
| 5,598,848 A | 2/1997 | Swanson et al. | |
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,893,885 A | 4/1999 | Webster, Jr. | |
| 5,897,553 A | 4/1999 | Mulier et al. | |
| 5,954,649 A | 9/1999 | Chia et al. | |
| 5,954,719 A * | 9/1999 | Chen ................. | A61B 18/1206 606/34 |
| 6,004,269 A | 12/1999 | Crowley et al. | |
| 6,012,457 A | 1/2000 | Lesh | |
| 6,016,437 A | 1/2000 | Tu et al. | |
| 6,024,740 A | 2/2000 | Lesh et al. | |
| 6,063,098 A * | 5/2000 | Houser ............ | A61B 17/22012 606/169 |
| 6,073,048 A | 6/2000 | Kieval et al. | |
| 6,096,037 A | 8/2000 | Mulier et al. | |
| 6,117,101 A | 9/2000 | Diederich et al. | |
| 6,142,992 A * | 11/2000 | Cheng ................ | A61B 18/1206 606/34 |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,245,065 B1 * | 6/2001 | Panescu ............ | A61B 18/1206 606/40 |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,322,559 B1 | 11/2001 | Daulton et al. | |
| 6,460,545 B2 | 10/2002 | Kordis | |
| 6,522,926 B1 | 2/2003 | Kieval et al. | |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,656,174 B1 | 12/2003 | Hedge et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 9,022,948 B2 | 5/2015 | Wang | |
| 2002/0068885 A1 | 6/2002 | Harhen et al. | |
| 2002/0120304 A1 | 8/2002 | Mest | |
| 2002/0151884 A1 | 10/2002 | Hoey et al. | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0127963 A1 | 7/2004 | Uchida et al. | |
| 2004/0215186 A1 | 10/2004 | Cornelius et al. | |
| 2005/0010206 A1 | 1/2005 | Nasab et al. | |
| 2005/0288730 A1 | 12/2005 | Deem et al. | |
| 2006/0089678 A1 | 4/2006 | Shalev | |
| 2007/0135875 A1 | 6/2007 | Demarais et al. | |
| 2008/0255478 A1 | 10/2008 | Burdette | |
| 2009/0076409 A1 | 3/2009 | Wu et al. | |
| 2009/0192507 A1 | 7/2009 | Luttich | |
| 2010/0016762 A1 | 1/2010 | Thapliyal et al. | |
| 2010/0094209 A1 | 4/2010 | Drasler et al. | |
| 2010/0168737 A1 | 7/2010 | Grunewald | |
| 2010/0249773 A1 | 9/2010 | Clark et al. | |
| 2010/0268307 A1 | 10/2010 | Demarais et al. | |

(56) References Cited

U.S. PATENT DOCUMENTS

| | | | |
|---|---|---|---|
| 2010/0286684 | A1 | 11/2010 | Hata et al. |
| 2011/0004087 | A1 | 1/2011 | Fish et al. |
| 2011/0118726 | A1 | 5/2011 | de la Rama et al. |
| 2011/0137298 | A1 | 6/2011 | Nguyen et al. |
| 2011/0152857 | A1 | 6/2011 | Ingle |
| 2011/0160720 | A1 | 6/2011 | Johnson |
| 2011/0213231 | A1 | 9/2011 | Hall et al. |
| 2011/0257641 | A1 | 10/2011 | Hastings et al. |
| 2011/0264011 | A1 | 10/2011 | Wu et al. |
| 2011/0264086 | A1 | 10/2011 | Ingle |
| 2011/0270247 | A1* | 11/2011 | Sherman ............ A61B 18/1492 606/41 |
| 2012/0101538 | A1* | 4/2012 | Ballakur ................ A61B 18/10 607/3 |
| 2012/0136350 | A1* | 5/2012 | Goshgarian ........ A61B 18/1492 606/41 |
| 2012/0143097 | A1 | 6/2012 | Pike, Jr. |
| 2012/0143298 | A1 | 6/2012 | Just et al. |
| 2012/0296232 | A1 | 11/2012 | Ng |
| 2012/0323233 | A1 | 12/2012 | Maguire et al. |
| 2013/0116737 | A1 | 5/2013 | Edwards et al. |
| 2013/0131743 | A1 | 5/2013 | Yamasaki et al. |
| 2013/0144251 | A1 | 6/2013 | Sobotka |
| 2013/0172715 | A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Dibona, Gerald F., Neural Control of the Kidney: Past, Present, and Future, Hypertension Journal of the American Heart Association, vol. 41, Mar. 2003, Part II, 621-624.

Dibona, Gerald F., Renal Innervation and Denervation: Lessons from Renal Transplantation Reconsidered, Artificial Organs, vol. 11, No. 6, 1987, 457-462.

Dibona, Gerald F., Role of the Renal Nerves in Renal Sodium Retention and Edema Formation, Trans Am Clin Climatol Assoc. 1990; 101: 38-45.

Dibona, Gerald F., Sympathetic Nervous System and Hypertension, Hypertension Journal of the American Heart Association, 2013; 61: 556-560.

Dibona, Gerald F., Sympathetic Nervous System and the Kidney in Hypertension, Curr Opin Nephrol Hypertens. Mar. 2002;11(2):197-200.

Dibona, Gerald F., The Sympathetic Nervous System and Hypertension, Hypertension Journal of the American Heart Association, Vo. 43, Feb. 2004, 147-150.

Doumas, Michael et al, Interventional Management of Resistant Hypertension, The Lancet, vol. 373, Apr. 11, 2009, pp. 1228-1230.

Dubuc, Marc et al, Feasibility of Cardiac Cryoablation Using a Transvenous Steerable Electrode Catheter, Journal of Interventional Cardiac Electrophysiology, 1998, 2: 285-292.

Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.

Esler, M. et al, Sympathetic Nerve Activity and Neurotransmitter Release in Humans: Translation from Pathophysiology into Clinical Practice, Scandinavian Physiological Society, 2003, 177, 275-284.

Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.

Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.

Evelyn, Kenneth A. et al, Effect of Thoracolumbar Sympathectomy on the Clinical Course of Primary (Essential) Hypertension, American Journal of Medicine, Feb. 1960, 188-221.

Freyberg, R. H. et al, The Effect on the Kidney of Bilateral Splanchnicectomy in Patients with Hypertension, The Journal of Clinical Investigation, vol. 16, Issue 1, Jan. 1937, 49-65.

Gafoor, Sameer et al, Nonresponders to Renal Denervation for Resistant Hypertension, Endovascular Today, Oct. 2013, 63-70.

Garel, L. et al, Fatal Outcome After Ethanol Renal Ablation in Child with End-Stage Kidneys; AJR 146:593-594, Mar. 1986.

Gazdar, A. F. et al, Neural Degeneration and Regeneration in Human Renal Transplants, The New England Journal of Medicine, vol. 238, No. 5, Jul. 1970, 222-224.

Goldberg, Michael R. et al, Reconstructive Vascular Surgery for Renovascular Hypertension, Can Med Assoc J. Feb. 2, 1974;110(3):275-80.

Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.

Gorisch, Wolfram et al, Heat-Induced Contraction of Blood Vessels, Lasers in Surgery and Medicine 2:1-13 (1982).

Grassi, Guido et al, Baroreflex Control of Sympathetic Nerve Activity in Essential and Secondary Hypertension, Hypertension Journal of The American Heart Association, 1998;31:68-72.

Grassi, Guido et al, Dissociation Between Muscle and Skin Sympathetic Nerve Activity in Essential Hypertension, Obesity, and Congestive Heart Failure, Hypertension. 1998;31:64-67.

Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.

Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.

Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.

Guyton, Arthur C., Blood Pressure Control Special Role of the Kidneys and Body Fluids, Science, vol. 252, Jun. 1991, 1813-1816.

Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.

Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.

Hall, J.E. et al, Role of Sympathetic Nervous System and Neuropeptides in Obesity Hypertension, Brazilian Journal of Medical and Biological Research, 2000, 33:605-618.

Hall, John E., The Kidney, Hypertension, and Obesity, Hypertension. 2003;41:625-633.

Hall, Winthrop H. et al, Combined Embolization and Percutaneous Radiofrequency Ablation of a Solid Renal Tumor, American Journal of Roentgenology, 174, Jun. 2000, 1592-1594.

Hamm, Christian et al, Confluence, Issue eight, Apr. 2014.

Han, Young-Min et al, Renal Artery Embolization with Diluted Hot Contrast Medium: An Experimental Study, Journal of Vascular and Interventional Radiology, Jul. 2001;12(7):862-868.

Hansen, Jesper Melchoir et al, The Transplanted Human Kidney Does Not Achieve Functional Reinnervation, Clinical Science, (1994) 87, 13-20.

(56) References Cited

OTHER PUBLICATIONS

Heuer, George J., The Surgical Treatment of Essential Hypertension, Annals of Surgery, Oct. 1936, vol. 104, No. 3, 771-786.

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of The American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.

Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoei K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of the American Heart Association, 1998;32:249-254.

Humpreys, Michael H., Renal Nerves and CKD: Is Renal Denervation the Answer?, Journal of the American Socity of Nephrology, 2012, 23: 1-3.

International Search Report and Written Opinion for Application No. PCT/US2010/054637 dated Jan. 3, 2011.

International Search Report and Written Opinion for Application No. PCT/US2010/054684 dated Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Jin, Yu et al, No Support for Renal Denervation in a Meta-Analysis, JACC vol. 62, No. 21, 2013 Correspondence Nov. 19/26, 2013:2029-30.

Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the SYMPLICITY HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part 2 Apr. 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, the Role of Renal Sympathetic Nerves in Hypertension: Has Percutaneous Renal Denervation Refocused Attention on Their Clinical Significance?; Progress in Cardiovascular Disease 52 (2009) 243-248.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, Ge et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.

(56) References Cited

OTHER PUBLICATIONS

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. February 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After Symplicity HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/Jun.), 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of the American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of the American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, Pace, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II,II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.

(56) References Cited

OTHER PUBLICATIONS

Oral, Hakan et al, Pulmonary Vein Isolation for Paroxysmal and Persistent Atrial Fibrillation, Circulation Journal of the American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14 (4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of the American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569572.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Zazgornik, Jan et al, Bilateral Nephrectomy: The Best, but Often Overlooked, Treatment for Refractory Hypertension in Hemodialysis Patients, AJH 1998; 11:1364-1370.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.

(56) References Cited

OTHER PUBLICATIONS

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Smith, Harold P. et al, Radiofrequency Neurolysis in a Clinical Model Neuropathological Correlation, J Neurosurg 55:246-253, 1981.

Smithwick, R.H., An Evaluation of the Surgical Treatment of Hypertension, The Bulletin, Nov. 1949; 25(11):698-716.

Smithwick, Reginald H. et al, Splanchnicectomy for Essential Hypertension, The Journal of the American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.

Sowers, James R. et al, Diabetes, Hypertension, and Cardiovascular Disease: An Update, Hypertension Journal of The American Heart Association, 2001;37:1053-1059.

Stanley, James C., Surgical Treatment of Renovascular Hypertension, The American Journal of Surgery, vol. 174, Aug. 1997, 102-110.

Stella, Andrea et al, Effects of Reversible Renal Denervation on Haemodynamic and Excretory Functions of the Ipsilateral and Contralateral Kidney in the Cat, Journal of Hypertension 1986, 4: 181-188.

Stuart, Candace, Newest Frontier in Cardiac Care: Kidneys; Cardiovascular Business, Dec. 13, 2012.

Stuart, Mary, Masterminds of Ardian: An Interview With Inventors Mark Gelfand and Howard Levin, Windhover Information, Start-Up Jan. 1, 2011.

Sun, Yingxian et al, Risk of Coronary Stenosis with Venous Ablation for Epicardial Accessory Pathways, PACE, Apr. 2001, Part II, vol. 24, 605.

Swartz, John F. et al, Radiofrequency Endocardial Catheter Ablation of Accessory Atrioventricular Pathway Atrial Insertion Sites, Circulation Journal of The American Heart Association, 1993;87:487-499.

Teigen, Corey L. et al, Segmental Renal Artery Embolization for Treatment of Pediatric Renovascular Hypertension, Journal of Vascular and Interventional Radiology, 1992; 3:111-117.

Teixeira, Maria Do Carmo et al, 1992; Role of the Peripheral Renin Profile in Predicting Blood Pressure Control After Bilateral Nephrectomy in Renal-Transplanted Patients, Nephrol Dial Transplant (1998) 13: 2092-2097.

Teo, W S et al, Radiofrequency Catheter Ablation of Accessory Pathways: The Initial Experience in Singapore, Singapore Medical Journal, 1994; vol. 35:36-40.

Thiebot, J. et al, Bilateral Nephrectomy by Embolization of the Renal Arteries: A Report on Five Cases (author's transl), Sem Hop. Apr. 8-15, 1980;56(13-14):670-5.

Thomas, George et al, Renal Denervation to Treat Resistant Hypertension: Guarded Optimism, Cleveland Clinic Journal of Medicine, vol. 79, No. 7, Jul. 2012, 501-510.

Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.

Ting, Chih-Tai et al, Arterial Hemodynamics in Human Hypertension Effects of Angiotensin Converting Enzyme Inhibition, Hypertension Journal of The American Heart Association, 1993;22:839-846.

Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.

Valente, John F. et al, Laparoscopic Renal Denervation for Intractable ADPKD-Related Pain, Nephrol Dial Transplant (2001) 16:160.

Villarreal, Daniel et al, Effects of Renal Denervation on Postprandial Sodium Excretion in Experimental Heart Failure, American Journal of Physiology, May 1994;266(5 Pt 2):R1599-R1604.

Vonend, Oliver et al, Secondary Rise in Blood Pressure After Renal Denervation, The Lancet, vol. 380, Issue 9843, p. 778, Aug. 25, 2012.

Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.

Webb, R.L. et al, Functional Identification of the Central Projections of Afferent Renal Nerves, Clin. and Exper. Theory and Practice, Ag(SUPPL.I), 47-57 (1987).

Weinstock, Marta et al, Renal Denervation Prevents Sodium Retention and Hypertension in Salt-Sensitive Rabbits with Genetic Baroreflex Impairment, Clinical Science (1996) 90, 287-293.

Wilcox, Josiah N., Scientific Basis Behind Renal Denervation for the Control of Hypertension, Medtronic, Inc., Dec. 2012, 38 pages.

Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.

Wolf-Maier, Katharina et al, Hypertension Treatment and Control in Five European Countries, Canada, and the United States, Hypertension. 2004;43:10-17.

Worthley, Stephen G. et al, Renal Denervation: How Do You Measure Success?, presentation 28 pages; Jul. 30, 2013.

Wyss, J.M. et al, Sensory Denervation of the Kidney Attenuates Renovascular Hypertension in the Rat, Am J Physiol Heart Circ Physiol 250:H82-H86, 1986.

International Search Report and Written Opinion for Application No. PCT/US14/023221 dated Aug. 22, 2014.

International Search Report and Written Opinion for Application No. PCT/US14/023248 dated Jun. 4, 2014.

Abboud, Francois M., The Sympathetic System in Hypertension, State-of-the-Art Review, Hypertension Journal of The American Heart Association, Hypertension 4 (suppl II): II-208-II-225, 1982.

Allen, Edgar V., Sympathectomy for Essential Hypertension, Circulation Journal of The American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of The American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.

Arentz, Thomas et al, Feasibility and Safety of Pulmonary Vein Isolation Using a New Mapping and Navigation System in Patients with Refractory Atrial Fibrillation, Circulation Journal of The American Heart Association, Nov. 18, 2003, 2484-2490.

Badoer, Emilio et al, Cardiac Afferents Play the Dominant Role in Renal Nerve Inhibition Elicited by Volume Expansion in the Rabbit, American Journal of Physiology, 1998, R383-R388.

Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.

Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.

Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.

(56) References Cited

OTHER PUBLICATIONS

Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9:741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987 ;74(1):14-8.
Chabanier, H. et al, on the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of The American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews, vol. 81, No. 4, Oct. 2001.
Dequattro V. et al, The Sympathetic Nervous System: The Muse of Primary Hypertension, Journal of Human Hypertension, 2002, 16(Supp 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.

\* cited by examiner

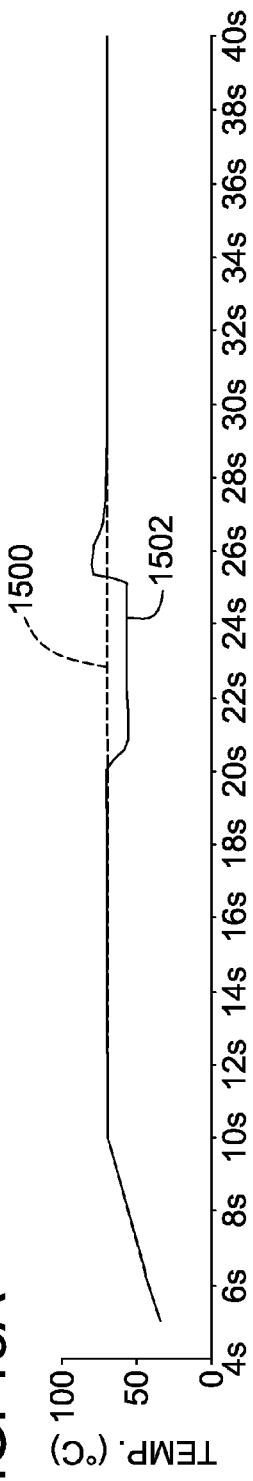
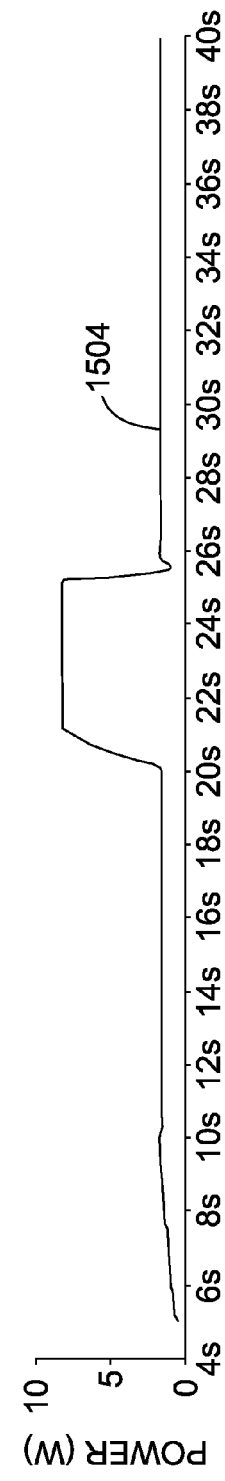
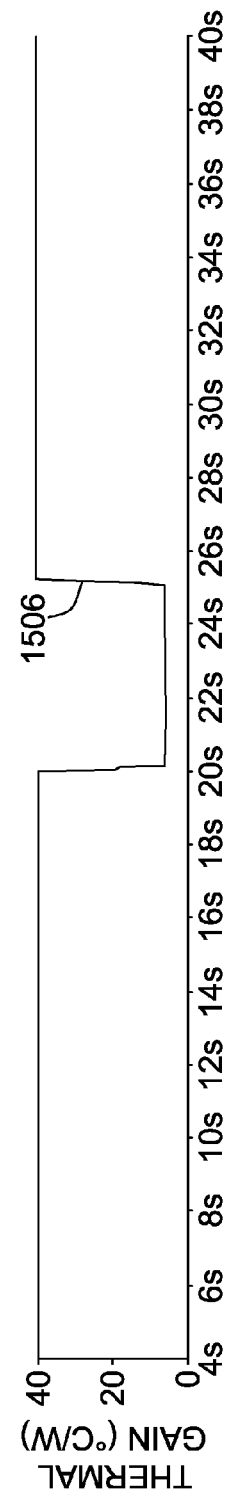
FIG. 15A
FIG. 15B
FIG. 15C

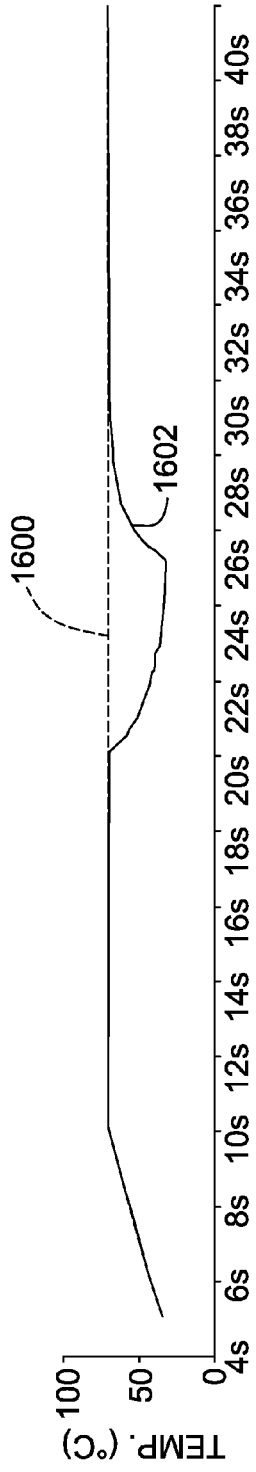
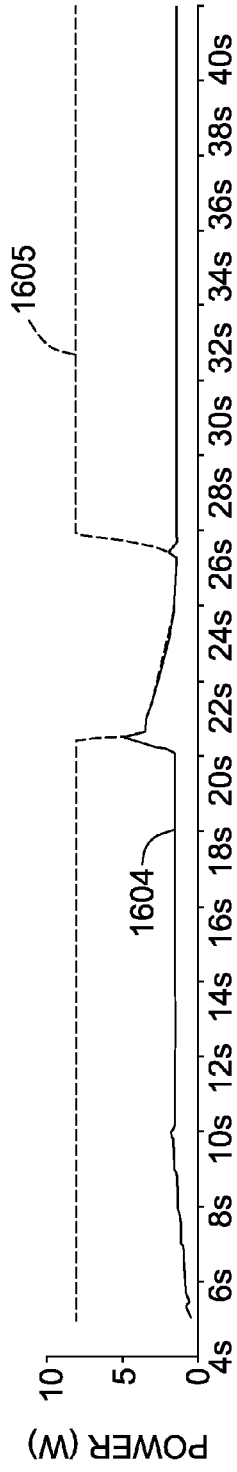
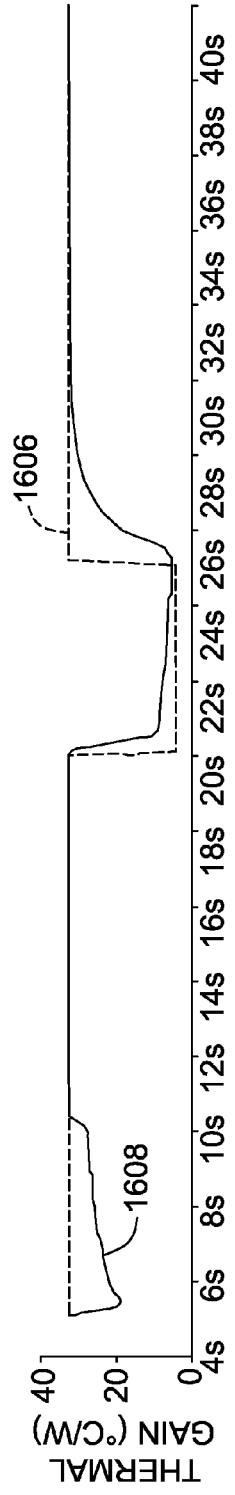
FIG. 16A
FIG. 16B
FIG. 16C

ABLATION SYSTEM, METHODS, AND CONTROLLERS

CROSS-REFERENCE TO RELATED APPLICATIONS

This application claims priority to provisional application Ser. No. 61/788,012, filed Mar. 15, 2013, and to provisional application Ser. No. 61/817,550, filed Apr. 30, 2013, and to provisional application Ser. No. 61/817,561, filed Apr. 30, 2013, each of which is incorporated herein in its entirety.

BACKGROUND OF THE DISCLOSURE a. Field of the Disclosure

The present disclosure relates generally to ablation systems, methods, and controllers. More particularly, the present disclosure relates to multi-electrode ablation systems, methods, and controllers.

b. Background Art

It is known that ablation systems are used to perform ablation procedures to treat certain conditions of a patient. A patient experiencing arrhythmia, for example, may benefit from ablation to prevent irregular heart beats caused by arrhythmogenic electric signals generated in cardiac tissues. By ablating or altering cardiac tissues that generate such unintended electrical signals, the irregular heart beats may be stopped. Ablation systems are also known for use in treating hypertension in patients. In particular, renal ablation systems, also referred to as renal denervation systems, are used to create lesions along the renal sympathetic nerves—a network of nerves that help control blood pressure. The intentional disruption of the nerve supply has been found to cause blood pressure to decrease.

Known techniques for renal denervation typically connect a radio frequency ("RF") generator to a catheter. The catheter is inserted in the renal artery and RF energy is emitted through an electrode in the distal end of the catheter to heat the renal nerves to a temperature that reduces the activity of renal nerve(s) near the electrode. The electrode is repositioned to several locations around the inner circumference and the length of the artery during the process. Some renal denervation systems utilize a catheter with more than one electrode in order to reduce the number of times that the catheter must be repositioned during the denervation procedure. Some of these systems apply RF energy to the multiple electrodes sequentially, while others apply the RF energy to all of the electrodes simultaneously. In some systems that separately control the RF energy delivered to multiple electrodes, multiple power supplies are used to provide the RF energy to the electrodes.

Moreover, ablation is achieved by applying heat to the selected area(s) over time. Thus, it is important to regulate the amount of heat, and more particularly the temperature at each electrode, during treatment of the patient. Mechanical differences between electrodes, dissimilar contact qualities between the electrodes and the treatment area (e.g., the artery wall when using a renal denervation system), and other factors result in different power levels being required for each of the multiple electrodes to achieve a desired temperature set-point.

There is a need, therefore, for multi-electrode ablation systems that operate multiple electrodes simultaneously, efficiently, and accurately to regulate the temperature at the electrodes.

BRIEF SUMMARY OF THE DISCLOSURE

In one aspect, a multi-electrode ablation system includes a power supply configured to be coupled to a plurality of electrodes and a controller coupled to the power supply. The controller is configured to determine a thermal gain of each electrode of the plurality of electrodes. For each electrode of the plurality of electrodes, the controller sets a power limit based at least in part on said electrode's determined thermal gain. The power limit establishes a maximum power that may be dissipated through said electrode.

In another aspect, a method of operating a multi-electrode ablation system includes determining a thermal gain of each electrode of a plurality of electrodes, and for each electrode of the plurality of electrodes, setting a power limit based at least in part on said electrode's determined thermal gain. The power limit establishes a maximum power that may be dissipated through said electrode.

In another aspect, a multi-electrode ablation system includes a power supply configured to be coupled to a plurality of electrodes and a controller coupled to the power supply. The controller is configured to set a power limit for each electrode of the plurality of electrodes, determine a thermal gain of each electrode of the plurality of electrodes, and determine, for each electrode, whether or not to reduce the power limit for that electrode based at least in part on the determined thermal gain of that electrode. The power limit establishes a maximum power that may be dissipated through the electrode.

In one aspect, a method of operating a multi-electrode ablation system includes setting a power limit for each electrode of a plurality of electrodes, determining a thermal gain of each electrode of the plurality of electrodes, and determining, for each electrode, whether or not to reduce the power limit for that electrode based at least in part on the determined thermal gain of that electrode. The power limit establishes a maximum power that may be dissipated through an electrode.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 15A is a graph of a temperature set-point and an electrode temperature during a computer simulated ablation.

FIG. 15B is a graph of the power applied to the electrode during the simulated ablation shown in FIG. 15A.

FIG. 15C is a graph of the thermal gain of the electrode during the simulated ablation shown in FIG. 15A FIG. 16A is a graph of a temperature set-point and an electrode temperature during a computer simulated ablation.

FIG. 16B is a graph of the power applied to the electrode and a power limit during the simulated ablation shown in FIG. 16A.

FIG. 16C is a graph of the actual thermal gain of the electrode and the calculated thermal gain of the electrode during the simulated ablation shown in FIG. 16A.

Corresponding reference characters indicate corresponding parts throughout the drawings.

DETAILED DESCRIPTION OF THE DRAWINGS

Figure 1:
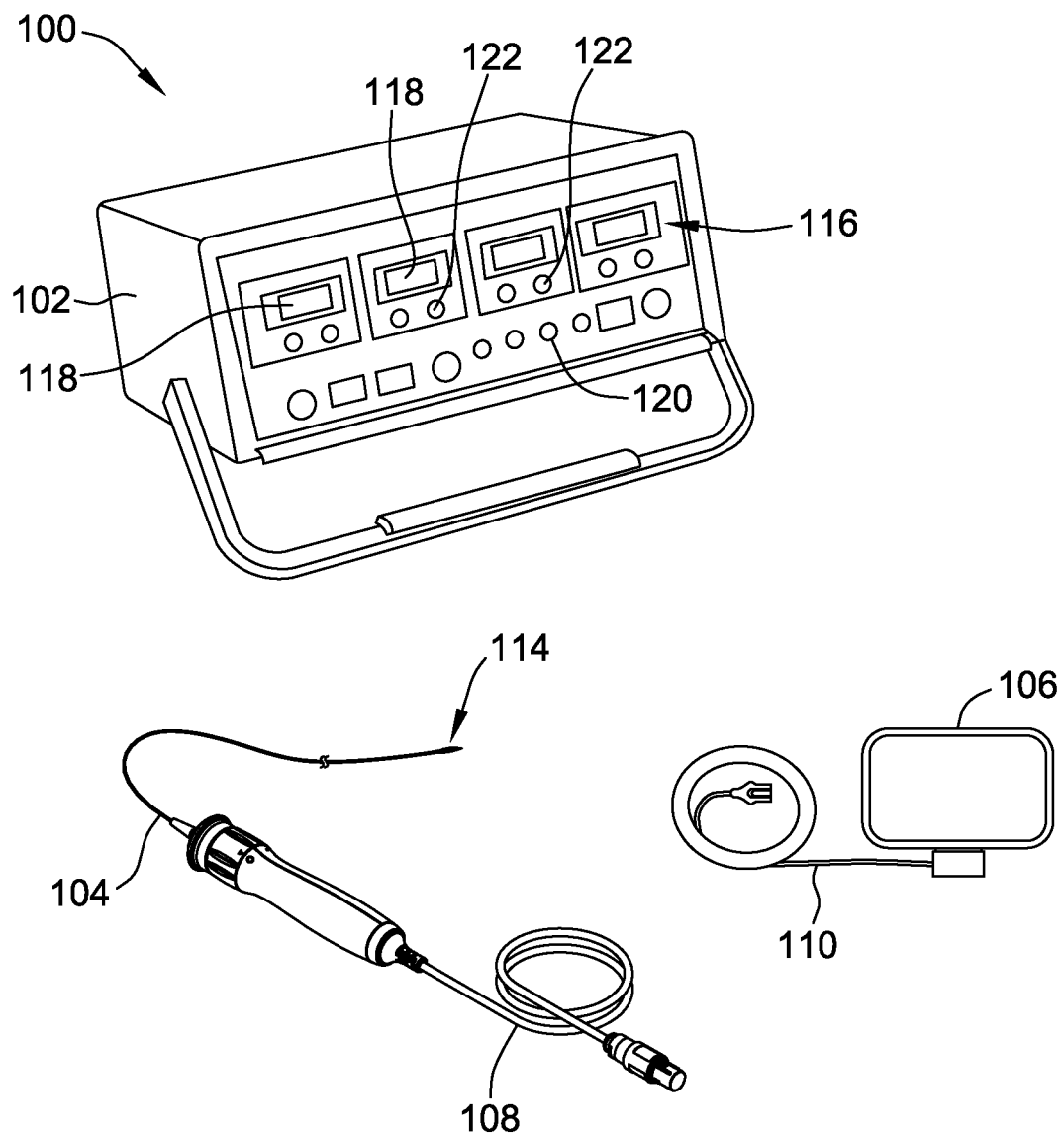
FIG. 1 is an isometric view of one embodiment of an ablation system including a generator, a catheter, and a return electrode.

This disclosure relates generally to ablation systems, methods, and controllers. More particularly, this disclosure relates to multi-electrode ablation systems, methods, and controllers. Still more particularly, this disclosure relates to multi-electrode renal ablation systems, methods, and controllers.

The methods and systems described herein provide accurate and efficient control of a multi-electrode ablation system. In general, various novel techniques for separately controlling when, how long, and how much energy to dissipate through each electrode in a multi-electrode system are described. For example, one exemplary system provides time-multiplexed simultaneous delivery of ablation power to multiple ablation electrodes with a single power supply. The energy required to meet the energy demand of each electrode is calculated and a duty cycle for each electrode is set accordingly. The output voltage of the single power supply is selected to provide sufficient power for the electrode with the highest energy demand. A common return path resistance is determined using a single current sensor in the return path of a multi-electrode ablation system and used to control one or more aspects of operation of the system.

Referring now to the drawings and in particular to FIGS. 1-4, an ablation system, generally indicated at 100, includes an ablation generator 102, a multi-electrode ablation catheter 104, and a return electrode 106. The ablation catheter 104 is removeably coupled to the ablation generator 102 by a cable 108. The return electrode 106 is removeably coupled to the ablation generator 102 by a cable 110. In use, the return electrode 106 is placed externally against a patient's body and the catheter 104 is inserted into the patient's body. Generally, the ablation generator 102 outputs radio frequency (RF) energy to the catheter 104 through the cable 108. The RF energy leaves the catheter 104 through a plurality of electrodes 112 (shown in FIG. 3) located at the distal end 114 of catheter 104. The RF energy travels through the patient's body to the return electrode 106. The dissipation of the RF energy in the body increases the temperature near the electrodes, thereby permitting ablation to occur. In the exemplary embodiment set forth herein, the ablation system 100 is a renal ablation system suitable for use in performing renal denervation. It is understood, however, that the ablation system may be used for other treatments without departing from the scope of this disclosure.

The generator 102 includes a user interface (UI) portion 116 for displaying information and notifications to an operator and receiving input from the user. Display devices 118 visually display information, such as measured temperatures, power output of the generator, temperature thresholds, cycle time, etc., and/or notifications to the user. Display devices 118 may include a vacuum fluorescent display (VFD), one or more light-emitting diodes (LEDs), liquid crystal displays (LCDs), cathode ray tubes (CRT), plasma displays, and/or any suitable visual output device capable of displaying graphical data and/or text to a user. The indicators 120 provide visual notifications and alerts to the user. In other embodiments, one or more of the indicators 120 provide audible notifications and/or alerts to the user. In the illustrated embodiment, indicators 120 are lights, such as light emitting diodes, incandescent lamps, etc. The indicators 120 may be turned on or off, for example, to indicate whether or not the generator 102 is receiving power, whether or not the catheter 104 is connected, whether or not the catheter (or all electrodes 112) are functioning properly, etc. Moreover, the indicators 120 may indicate a quality or degree of a feature or component of the system 100, such as by changing color, changing intensity, and/or changing the number of the indicators 120 that are turned on. Thus, for example, an indicator 120 may change color to represent a unitless notification of the quality of the contact between one or more of the electrodes 112 and an artery wall. UI portion 116 includes inputs 122, e.g., buttons, keys, knobs, etc., for receiving commands and/or requests from a user. In some embodiments, the UI portion 116, additionally or alternatively, displays a graphical user interface to a user, such as via one or more of the display device 118.

Figure 2:
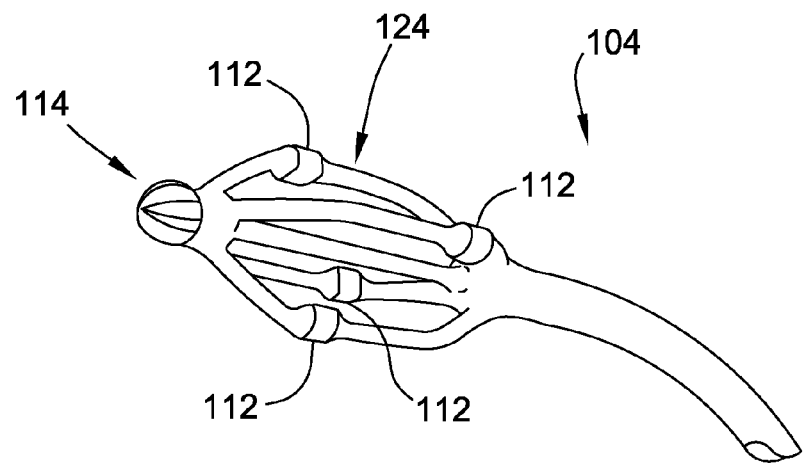
FIG. 2 is a partial view of a distal end of the catheter shown in FIG. 1.

As shown in FIG. 2, the multiple electrodes 112 may be disposed on a basket 124 located at the distal end 114 of the catheter 104. In the illustrated embodiment, basket 124 is an expandable basket that may be expanded and collapsed by an operator of the system 100 to position electrodes 112 against, for example, an artery wall. In the illustrated embodiment, the catheter 104 includes four electrodes 112. In other embodiments, the catheter 104 may include at least two, but other than four, electrodes 112. A thermocouple (not shown, also referred to herein as a temperature sensor) is attached to each electrode 112 provides temperature readings of the electrode. The catheter 104 also contains a thermistor (not shown) and a 1-Wire EEPROM. The generator 102 uses the thermistor for measuring ambient temperature and performing cold-junction compensation on the thermocouples. The EEPROM contains a unique ID which allows the generator 102 to reject devices not manufactured specifically for use with the generator 102. The generator 102 also maintains usage data on the EEPROM in order to enforce maximum operation limits for the catheter 104.

Figure 3:
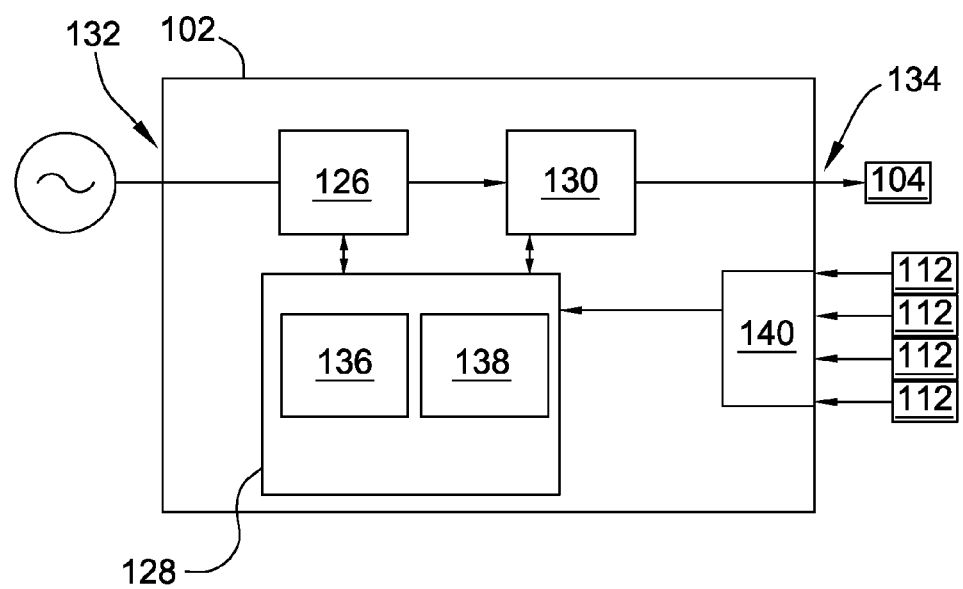
FIG. 3 is a schematic block diagram of a controller for use in the generator shown in FIG. 1.

Referring now to FIG. 3, generator 102 includes a power supply 126, a controller 128, and an RF output circuit 130. Power supply 126 receives AC power via an input 132 and converts the received power to a DC power output. The DC power output is provided to the RF output circuit 130 that outputs RF power to the catheter 104, and more specifically to the electrodes 112, via output 134. In the exemplary embodiment, power supply 126 includes a buck converter to provide a DC output of a lesser magnitude than the magnitude of the rectified AC power input. The controller 128 is coupled to and controls operation of the power supply 126 and the RF output circuit 130. As will be described in more detail below, the controller 128 controls operation of power supply 126 to cause the power supply to generate a desired output voltage, i.e. a DC output voltage having a magnitude determined by the controller 128. In other embodiments, the power supply 126 includes its own controller configured to control operation of the power supply 126 to generate the determined output voltage in response to a command from the controller 128. The controller 128 also controls operation of the RF output circuit 130. Controller 128 controls when and to which electrodes 112 the RF output circuit 130 couples its RF power output. In other embodiments, the RF output circuit 130 includes its own controller configured to control operation of the RF output circuit 130 in response to commands from the controller 128. In some embodiments, the RF output circuit 130 is part of, and integrated into, the power supply 126.

The controller 128 includes a processor 136 and a memory device 138 coupled to the processor 136. The term "processor" refers herein generally to any programmable system including systems and microcontrollers, reduced instruction set circuits (RISC), application specific integrated circuits (ASIC), programmable logic circuits, field programmable gate array (FPGA), gate array logic (GAL), programmable array logic (PAL), digital signal processor (DSP), and any other circuit or processor capable of executing the functions described herein. The above examples are exemplary only, and thus are not intended to limit in any way the definition and/or meaning of the term "processor." Moreover, although a single processor is illustrated in FIG. 3, the processor 136 may include more than one processor and the actions described herein may be shared by more than one processor.

The memory device 138 stores program code and instructions, executable by the processor 136. When executed by the processor 136, the program code and instructions cause the processor 136 to operate as described herein. The memory device 138 may include, but is not limited to only include, non-volatile RAM (NVRAM), magnetic RAM (MRAM), ferroelectric RAM (FeRAM), read only memory (ROM), flash memory and/or Electrically Erasable Programmable Read Only Memory (EEPROM). Any other suitable magnetic, optical and/or semiconductor memory, by itself or in combination with other forms of memory, may be included in the memory device 138. The memory device 138 may also be, or include, a detachable or removable memory, including, but not limited to, a suitable cartridge, disk, CD ROM, DVD or USB memory. Although illustrated separate from the processor 136, memory device 138 may be integrated with the processor 136.

Figure 4:
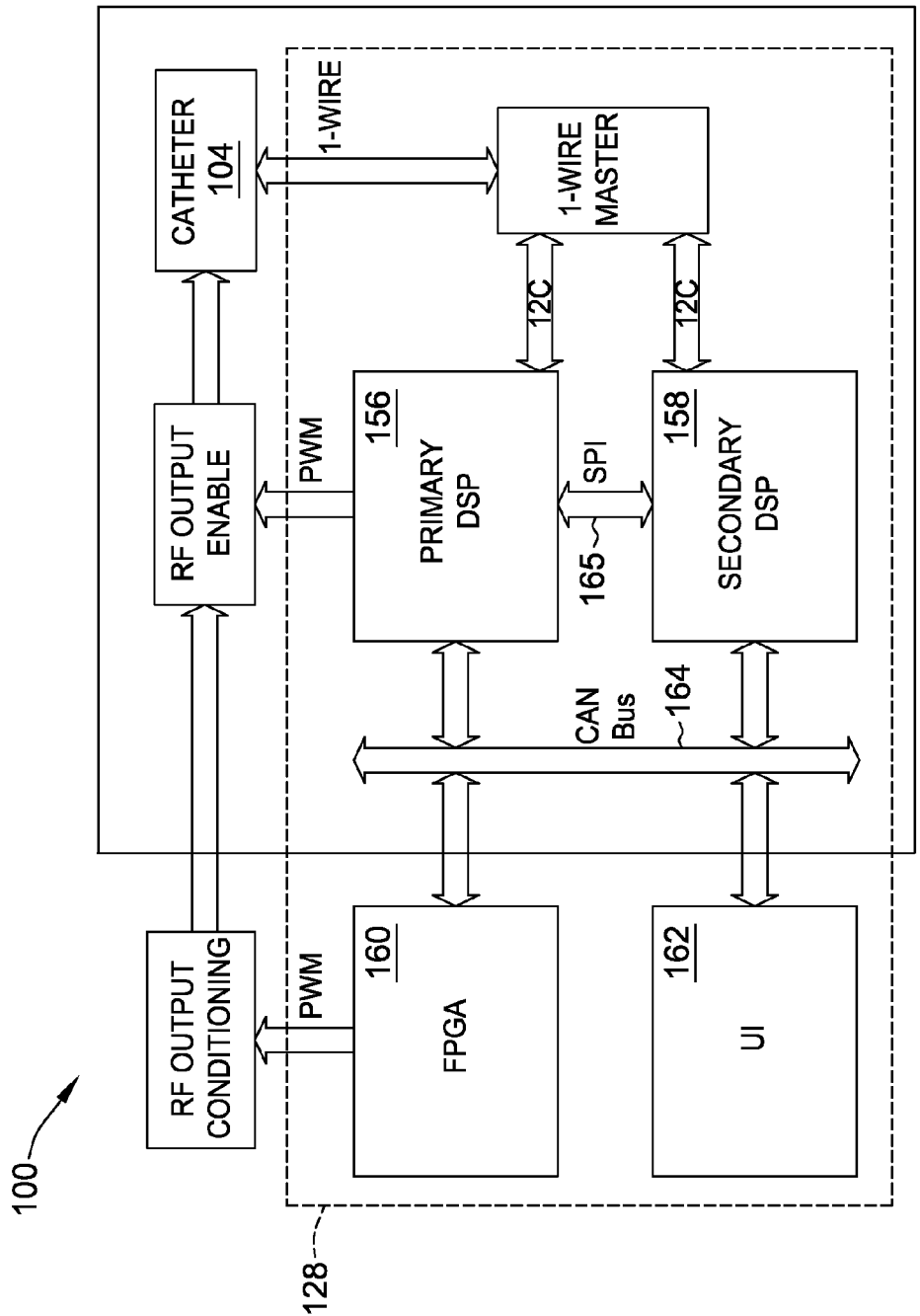
FIG. 4 is a functional block diagram of the ablation system shown in FIG. 1.

FIG. 4 is a functional block diagram of the ablation system 100. The controller 128 includes a primary DSP 156, a secondary DSP 158, and FPGA 160, and a user interface (UI) processor 162. The DSPs 156 and 158 control the temperature and output power delivered by the four ablation electrodes 112 contained in the catheter 104 by sending appropriate control signals to the FPGA 160. The FPGA 160 controls the power electronics (i.e., power supply 126 and RF output circuit 130), subject to control inputs from the UI processor 162. Both primary and secondary DSPs 156 and 158 communicate with the FPGA 160, the UI 162, and each other over a CAN bus 164. The primary and secondary DSPs 156 and 158 also communicate certain information to each other via a dedicated McBSP link 165.

In the illustrated embodiment, the UI processor 162 is responsible for presenting, such as via user interface portion 116, the current state of the system to the operator as well as providing a means for the operator to modify parameters such as ablation time and temperature. The UI processor 162 is also responsible for managing firmware upgrades, including the communication of new firmware images to the FPGA 160 and DSPs 156 and 158.

The FPGA 160 responds to control signals received from the primary DSP 156 via the CAN bus 164 to drive the power supply 126 and the RF output circuit 130 (specifically a buck regulator and an RF amplifier, respectively, in this implementation) that apply power to the catheter 104. It checks for periodic inputs from both the primary DSP 156 and the secondary DSP 158 in order to allow an RF output, and it monitors physical signals from an operator foot switch (not shown) and sends corresponding switch status updates to the DSPs 156 and 158 and to the UI processor 162.

The primary DSP 156 runs the main control loop, sampling the current, voltage, and temperature for each electrode, and adjusting the power delivered to each electrode to achieve the desired temperature, as will be described in more detail below. It is also the operating state master of the generator 102. While the operator interacts with the UI and with other physical components connected to the generator 102 in ways that may result in a generator state change, the primary DSP 156 ultimately decides the state of the generator 102.

The primary DSP 156 is supervised in its task by the secondary DSP 158, which ensures that patient safety limits are not breached. The secondary DSP 158 independently measures output power, temperature, and other parameters set by the primary DSP 156. The secondary DSP 158 also verifies that the software running on the primary DSP 156 is operational.

Figure 5:
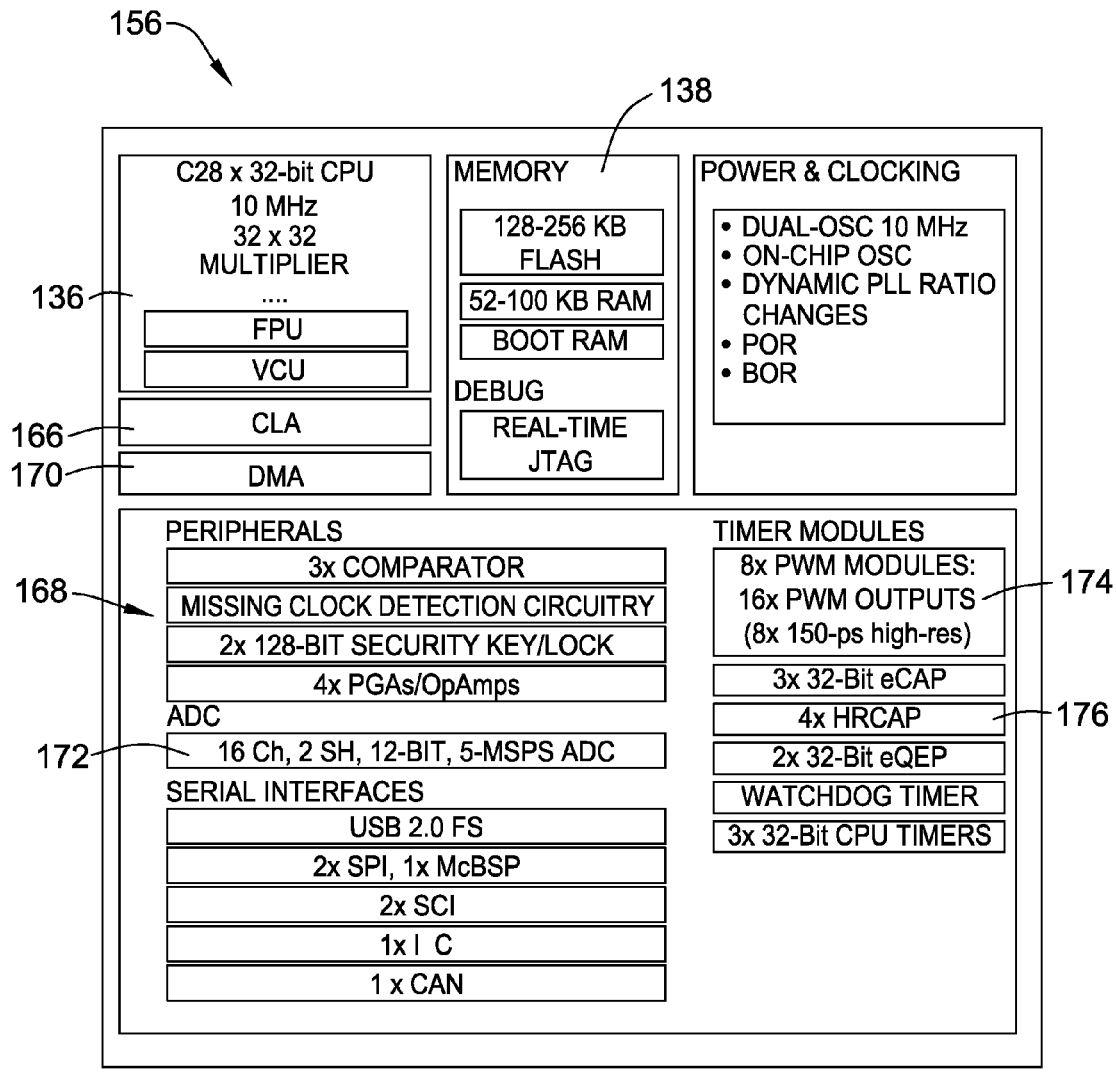
FIG. 5 is a digital signal processor (DSP) for use in the ablation system shown in FIG. 1.

FIG. 5 is a block diagram of the primary DSP 156. Secondary DSP 158 is substantially the same as the primary DSP 156 shown in FIG. 5. In the illustrated embodiment, both the primary and secondary DSPs 156 and 158 are 32-bit architecture microcontrollers each including a 32 bit processor 136. The DSP 156 supports a maximum clock frequency of 80 MHz and includes a floating-point unit (FPU) for native single-precision floating-point operations, a fully-programmable control law accelerator (CLA) 166 for offloading time-critical operations from the processor 136, and a Viterbi control unit (VCU) for supporting complex math operations. The DSPs 156 and 158 also include embedded memory 138. The DSPs 156 and 158 contain 4 types of memory: RAM, Flash, OTP (One-Time Programmable) and ROM. Flash memory is divided into 8 sectors of equal size, for a total size of 256 Kbytes. A small amount (1K 16-bit words) of OTP memory is provided for storage of code or data that should not be erasable. This typically includes data such as serial numbers and device-specific addresses. 32K 16-bit words of Boot ROM are provided, which contain boot code to initialize the processor 136, various trigonometric data tables, such as Sine, Cosine, Arc Tangent and Taylor series coefficients. Also available are functions to erase and program the Flash memory.

The DSPs 156 and 158 include a set of internal peripherals 168. In order to avoid burdening the processor 136 with simple I/O and communications data transfer, a DMA controller 170 is provided to manage access to the memory 138, analog-to-digital converter (ADC) 172, USB 173, pulse width modulator (PWM) modules 174, and McBSP. Data transfers to and from any of these peripherals are possible without processor 136 intervention, increasing data throughput through the system 100. The ADC 172 has two sample-and-hold circuits that can be sampled either simultaneously or sequentially. Each circuit is fed by one of 16 channels. The ADC 172 has 12-bit resolution. Both the primary DSP 156 and secondary DSP 158 use the ADC 172 to sample voltage, current, and thermocouple temperature for each electrode 112 as well as thermistor temperature and hand switch status.

For generating square waves with specific frequencies and duty cycles, the DSPs 156 and 158 each contain eight PWM modules 174, each PWM module 174 including two separate outputs. These modules are used for generating specific pulse trains. The PWM modules 174 are chained together by a clock synchronization scheme that allows them to operate as a single system when required. They support deadband generation with independent rising-edge and falling-edge delay control as well as PWM chopping by a high-frequency carrier signal. Also, several key registers controlling the PWM modules 174, including the time-base period and counter-compare registers, are able to be asynchronously updated without corruption or unwanted behavior through the use of shadow registers. The primary DSP 156 uses four PWM modules 174 to send on and off pulses to the pulse transformers (not shown) which provide power output to the four catheter electrodes 112. For each PWM module 174, on pulses are generated with one channel and off pulses with the other. In addition to being set for desired duty cycles, the compare values also include some overlap between channels to minimize the amount of time that no electrode 112 is connected to the output.

The DSPs 156 and 158 each include four high-resolution capture (HRCAP) modules 176 for taking high-resolution pulse width measurements. Each module includes a dedicated input capture pin, a 2-word FIFO for rising-edge captures, and a 2-word FIFO for falling-edge captures. The secondary DSP 158 uses the HRCAP modules 176 to measure the duty cycle of the output at each electrode.

The CLA 166 is an on-chip floating-point co-processor that has extensive access to the ADC 172 and PWM modules 174. The CLA 166 is intended to be capable of executing control loop software without intervention by the main processor 136, thereby freeing up processing bandwidth for other tasks. The CLA 166 has its own instruction set, with support for addition, subtraction, multiplication, reciprocal, and square root calculation of single-precision floating point operands in four 32-bit result registers. Conversion to and from floating point of 16 and 32-bit integers is supported as well as the usual logical operations including arithmetic and logical shift. Branches and loops are supported and the existence of an indirect addressing mode in addition to the standard direct mode facilitates the processing of structured data. Throughput is enhanced by the provision of instructions that perform concurrent operations, such as multiply with parallel subtract and the ADC's feature of raising an "early interrupt" when starting its conversion process makes it possible for a program task to time execution so as to use the converted result "just-in-time".

The CLA's programs consist of tasks or interrupt service routines, which are code sequences whose starting address is contained in the interrupt vector register of its associated interrupt. When this interrupt fires, typically due to an ADC 172 conversion start or completion, the task is scheduled and run. Communication with the processor 136 is effected either through shared data memory blocks, which are permanently readable and writable by both CLA 166 and processor 136, or by selectively mapping memory areas for use by the CLA 166, access being controlled by access bits previously set by the processor 136.

Figure 6:
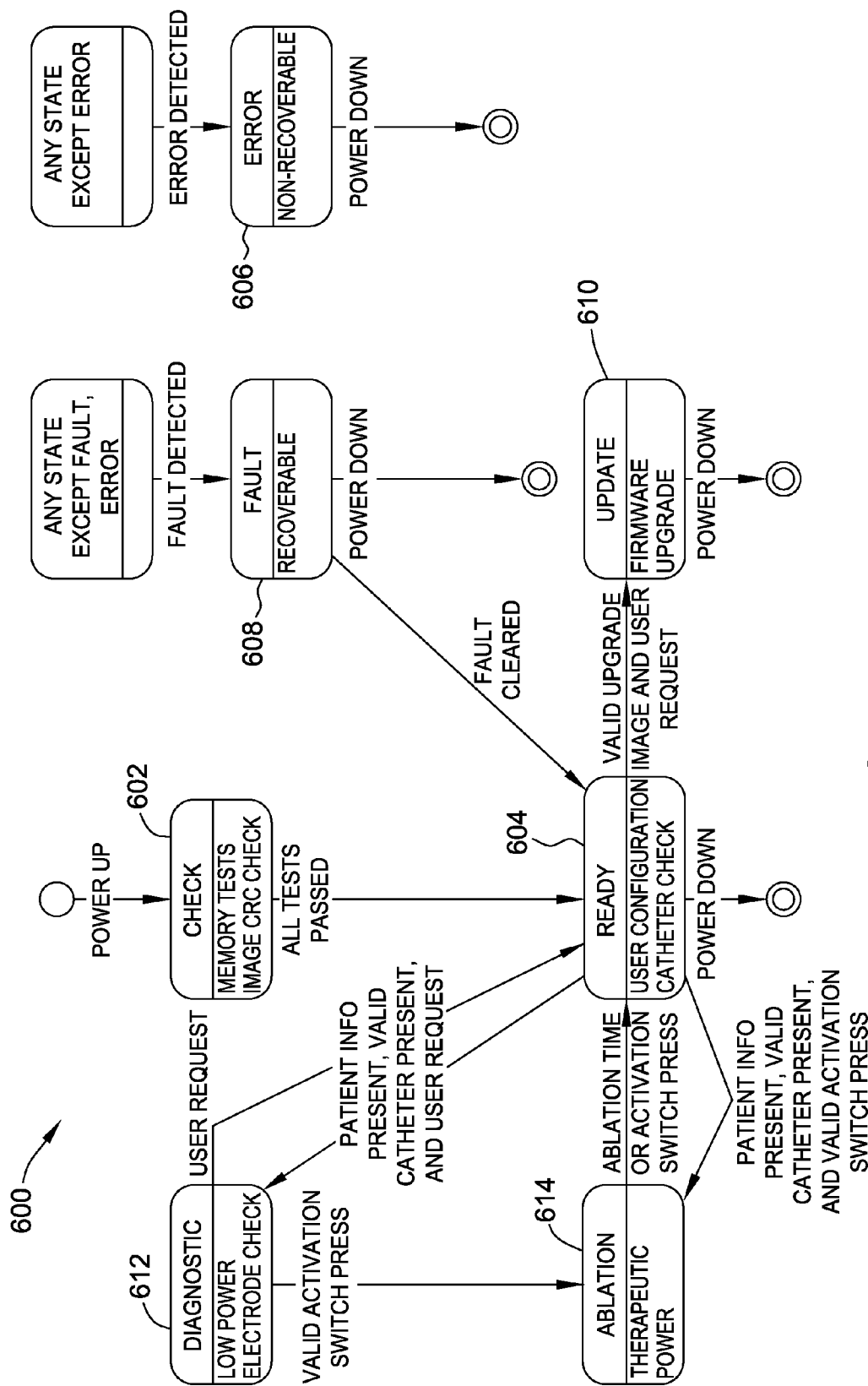
FIG. 6 is a diagram of the operating states of the system shown in FIG. 1.

Referring now to FIG. 6, which is a diagram of the operating states 600 of the ablation system 100, upon system power up the software enters a temporary testing state 602 where all required subsystems are tested for correct operation. Examples include RAM tests and a cyclic redundancy check (CRC) of the software executable image. If all tests complete successfully, the system changes to a ready state 604. While in the ready state, patient information is entered and ablation parameters are configured on the UI 116. Meanwhile, the DSP software is also checking for catheter 104 presence and validity.

If one or more tests in the Check state fail, the system 100 transitions to an error state 606. This is a non-recoverable state and can only be exited by a power cycle. Other errors detected in the system are treated either as nonrecoverable errors or as recoverable faults. If a recoverable fault occurs, the system transitions to a fault state 608. If a recoverable fault is cleared, the system transitions back to the ready state 604.

If an update is necessary and the DSP software is in the ready state 604, an update state 610 is entered, which disables all normal functionality and stores a new software image in flash memory. Once the new image has been successfully transferred, a power cycle is necessary to allow the new software to be loaded and run. If there is a communication issue during the image transfer or if the image is transferred but ends up being invalid after a CRC check (during testing state 602), the DSP software will request a retry from the UI 116. If a valid image is not successfully transferred after several retries, the system 100 will transition to the error state 606.

From the ready state 604, the system may transition to a diagnostic state 612 once a valid catheter 104 is connected, a message signifies that user configuration is complete, and a valid activation switch press is detected. During the diagnostic state 612, low-power measurements are taken in order to perform pre-ablation electrode 112 checks. The system 100 will be switched back to the ready state 604 on reception of a UI 116 message indicating that the operator has requested the transition.

If a valid activation switch press is detected while in the diagnostic state 612, the system will transition to the ablation state 614. In this state, all power and temperature control loops are activated, and the secondary DSP 158 performs its supervisory functions over the primary DSP 156. The system 100 transitions back to the ready state 604 if the configured ablation time is met (typically 90 seconds) or if an activation switch is pressed again.

The primary DSP 156 is the generator state machine "master." All state transitions are initiated by the primary DSP 156. If another processor desires that the generator transition to another state, it must first request that the primary DSP 156 make the transition. The secondary DSP 158 supervises the primary DSP 156 here as well and verifies that any state transition is valid.

The controller 128 is configured to control overall operation of the system 100 in concert with a user's instructions. In general, the controller 128 is configured, such as by instructions stored in the memory device 138, to simultaneously electrically couple the output voltage from the power supply 126 to electrodes 112 via the RF output circuit 130. Under some circumstances, such as because of a malfunction of the electrode, operator selection, etc., one or more of the electrodes 112 may be disabled and the disabled electrode(s) are not coupled to the output voltage.

The primary DSP 156 is responsible for regulating the temperature at each electrode 112, subject to oversight by the secondary DSP 158. With additional reference to FIGS. 7-12, the controller 128 and DSP 156 in particular, uses an outer loop 178 (shown in FIG. 7) based on temperature and an inner loop 180 (shown in FIG. 7) based on voltage to control system 100 using a plurality of fixed length output cycles 151 (shown in FIGS. 9-12). In the exemplary embodiment, each output cycle 151 lasts for five milliseconds. Other embodiments may use any other suitable length output cycle 151. As will be described in more detail below, each output cycle 151 includes a measurement period 150 during which various measurements are taken and an output period 154 during which the output voltage is coupled to one or more of the electrodes 112. If more than one electrode 112 is enabled, the measurement period 150 includes a plurality of measurement sub-periods, as will be described in more detail below.

Mechanical differences between electrodes 112, dissimilar contact qualities between the electrodes 112 and the artery wall, and other factors result in different power levels being required for each electrode 112 to achieve the same temperature set-point, e.g., a desired temperature to produce ablation. Generally, the primary DSP 156 controls temperature at each electrode 112 by modifying the output of a single buck regulator and exposing each of the electrodes 112 to the resulting output voltage for varying amounts of time (thus delivering varying amounts of energy to each of the electrodes 112). The same output voltage is applied to each of the electrodes 112. The energy dissipated through each electrode 112, and therefore the temperature generated adjacent the electrode 112, is determined by how long each electrode 112 is coupled to the output voltage. Because, the output cycle 151 lasts for a fixed length of time, the maximum energy that may be delivered to any electrode 112 is determined by the output voltage of power supply 126. By increasing the output voltage of power supply 126 in the inner loop 180, controller 128 increases the maximum amount of energy that may be dissipated through an electrode (in particular an electrode 112 that is coupled to the voltage for the entire output period). Similarly, decreasing the output voltage of the power supply 126 decreases the maximum power dissipation through the electrodes 112.

With respect to the outer loop 178 of the control system, the difference in desired temperature versus measured or actual temperature, i.e., a temperature difference, is used to determine a desired power for each electrode 112. Both the primary and secondary DSPs 156 and 158 (shown in FIG. 4) sample temperature values. Due to the limited number of sample-and-hold circuits in the ADC 172 (shown in FIG. 5), the DSPs 156 and 158 collect these measurements at times other than when the voltage and current sampling is taking place. Therefore, all temperature measurements occur in the output period 154 of the output cycle 151.

To minimize the amount of hardware duplication, four thermocouple outputs are connected to multiplexers 140 (shown in FIG. 3) controlled by GPIO pins on the DSPs 156 and 158. The output signal of the multiplexer 140 is appropriately conditioned before being fed as an input to the ADC 172. There are two multiplexers 140 and two conditioning circuits, one pair for each DSP 156 and 158. This allows a hardware failure for one DSP 156 or 158 to be caught by the other DSP 158 or 156. Because of settle time associated with multiplexing thermocouples, only one thermocouple is measured for each output cycle 151. In each output cycle 151 one of the temperature sensors is coupled to controller 128 through multiplexer 140. After the controller 128 samples the temperature sensor's signal, the multiplexer 140 switches its output to the next temperature sensor. The next temperature sensor is sampled during the next output cycle 151. Thus, the delay between thermocouple measurements in the illustrated embodiment is four output cycles 151. This delay is accounted for in the compensator's poles and zeroes. In other suitable embodiments, however, the thermocouple measurements may be sampled more or less frequently within the scope of the present disclosure.

In addition to the four thermocouples, a "calibration" channel on the multiplexer 140 is used to measure a zero offset value. This offset is then applied to the four actual thermocouple readings. To minimize the delay to which the compensator is exposed, this measurement is taken infrequently, and never while the system 100 is controlling the temperature. Each DSP's software also samples a thermistor and uses that measurement to calibrate for ambient temperature.

Figure 7:
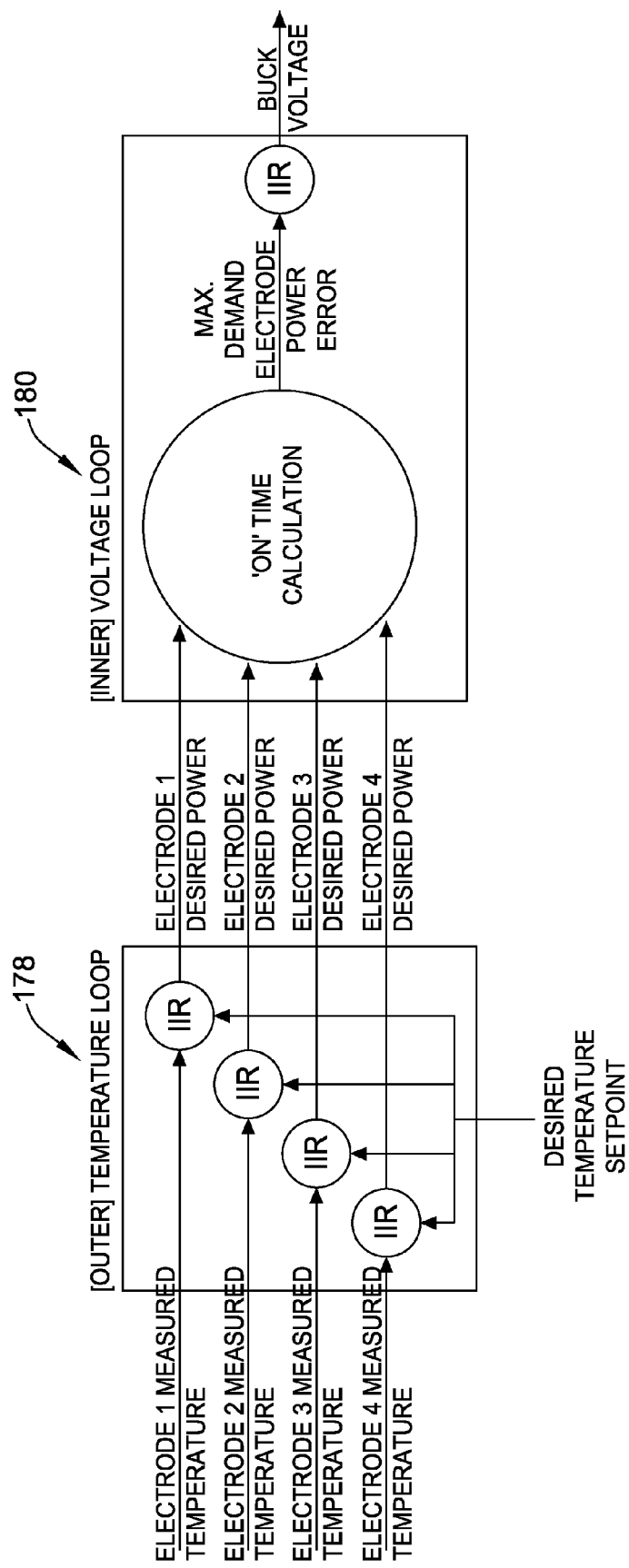
FIG. 7 is a diagram of a control cycle for use with the system shown in FIG. 1.

With reference to FIG. 7, to determine the desired power based on temperature difference, the primary DSP 156 uses an infinite impulse response (IIR) filter implementation of pole-zero compensation. The poles and zeroes for this compensator have been determined using analog modeling. When the generator is in diagnostic mode this portion of the control is bypassed and the desired power for each electrode 112 is simply 0.5 W.

In the inner loop 180, the controller 128 determines a target output voltage for the power supply 126 that will achieve the desired power delivery to the electrode 112 (sometimes referred to herein as the maximum demand electrode) that has the highest desired power determined in the outer loop 178. The energy that would be dissipated through the maximum demand electrode if it were coupled to the target output voltage for the entire output cycle 151 is determined. The target output voltage is determined based on the desired energy dissipation for the maximum demand electrode and an energy dissipation difference signal from a previous output cycle 151. The energy dissipation difference signal is the difference between the previous cycles desired energy dissipation through the maximum demand electrode and the actual energy dissipation through the maximum demand electrode. To determine the target output voltage for the buck regulator based on the difference, the primary DSP 156 uses an IIR filter implementation of pole-zero compensation. The poles and zeroes for this compensator have been determined using analog modeling. When the output cycle begins, the controller 128 causes the power supply 126 (shown in FIG. 3) to operate to produce the target output voltage.

Figure 9:
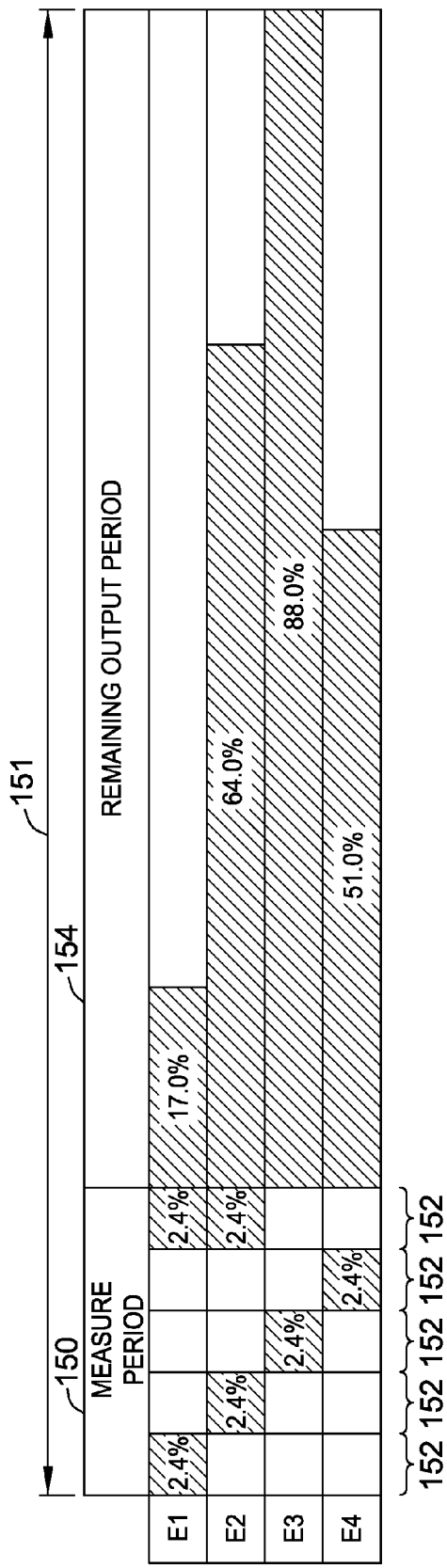
FIG. 9 is a diagram of an output cycle of the system shown in FIG. 1 with four electrodes enabled.
Figure 10:
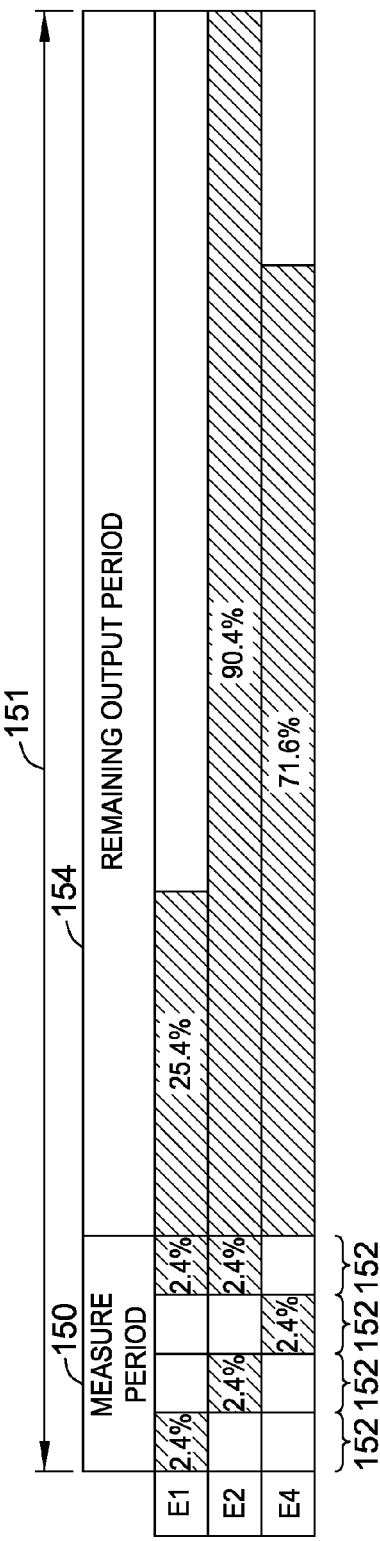
FIG. 10 is a diagram of an output cycle of the system shown in FIG. 1 with three electrodes enabled.
Figure 11:
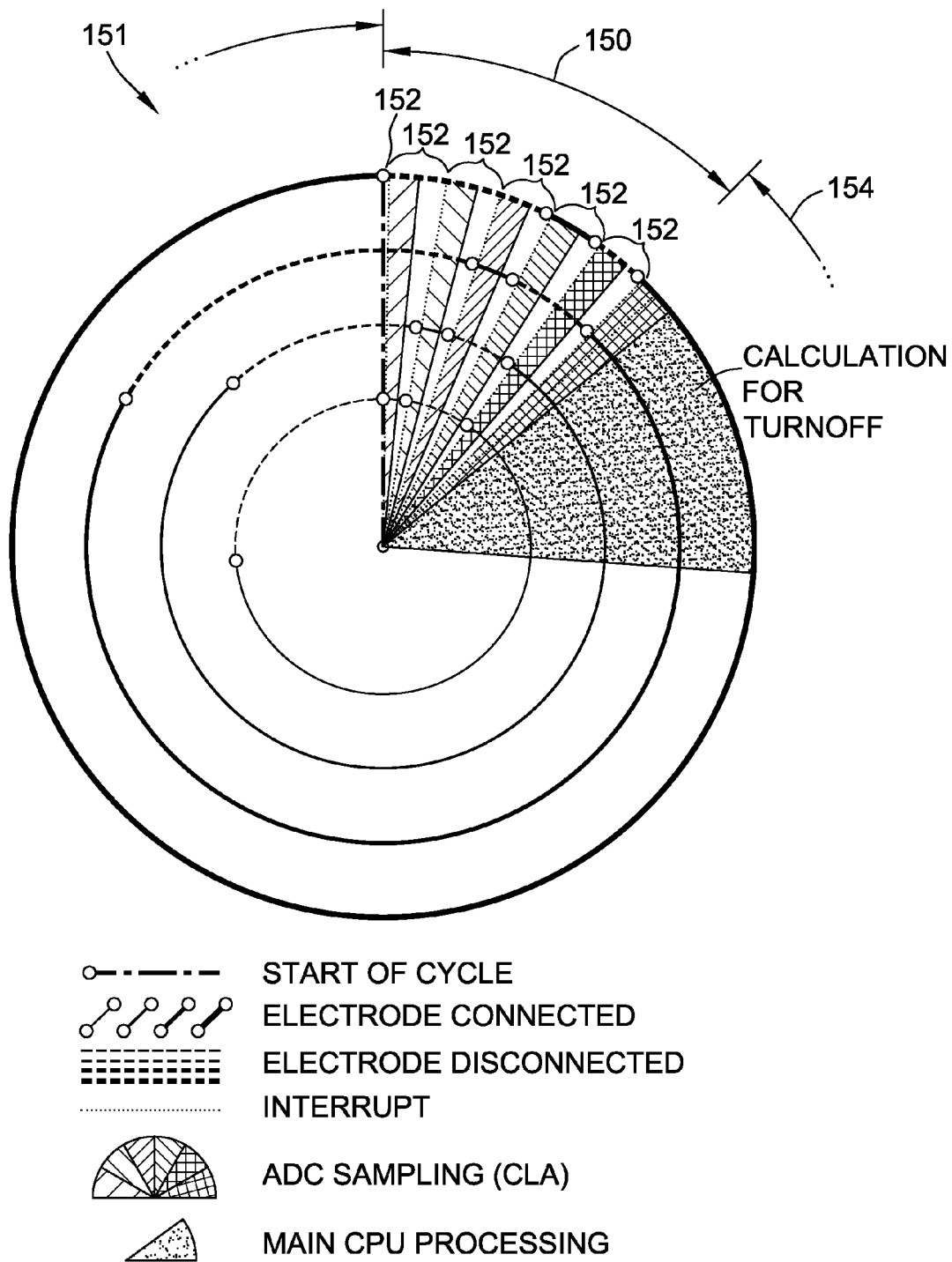
FIG. 11 is a graphical representation of an output cycle of the system shown in FIG. 1.

As described above, the target output voltage for the power supply 126 is determined in the inner loop 180 by the electrode 112 with the highest desired power, and the output duty cycle for that electrode 112 is the maximum possible duty cycle. Any electrode 112 with less demand is driven at a lower duty cycle, i.e., for less time in the output cycle 151. As may be best seen in FIGS. 9 and 10, the maximum duty cycle is a function of the number of enabled electrodes 112. Because of the measurements that need to be taken at the beginning of the output cycle 151, the output period 154 of the output cycle 151 is less than the entire output cycle 151. If only one electrode 112 is enabled, the maximum duty cycle is 100%. If more than one electrode 112 is enabled, the maximum duty cycle for an electrode 112 is reduced by the amount of time that the electrode 112 will need to be disconnected while measurements are being taken with other electrodes 112. Thus, the maximum duty cycle with four electrodes 112 enabled is 92.8% if the maximum demand electrode 112 is one of the electrodes 112 that is included in the combination measurement sub-period 152. In the example shown in FIG. 9, the maximum demand electrode 112 is not one of the electrodes 112 included in the combination measurement sub-period 152. If, as shown in FIG. 9, the maximum demand electrode is not part of the combination measurement sub-period 152, the maximum duty cycle is 90.4%. If only three electrodes 112 are enabled, the maximum duty cycle is 95.2% for the electrodes 112 in the combination measurement sub-period 152 and 92.8% for the electrode 112 not in the combination measurement sub-period 152.

The minimum duty cycle for an enabled electrode 112 is equal to the time that it must be connected to the output to take measurements at the beginning of the output cycle 151. If the required duty cycle for an electrode 112 is less than or equal to the electrode's minimum duty cycle, the electrode 112 will be connected for its minimum duty cycle during the measurement period 150 and will not be connected during the output period 154.

Figure 12:
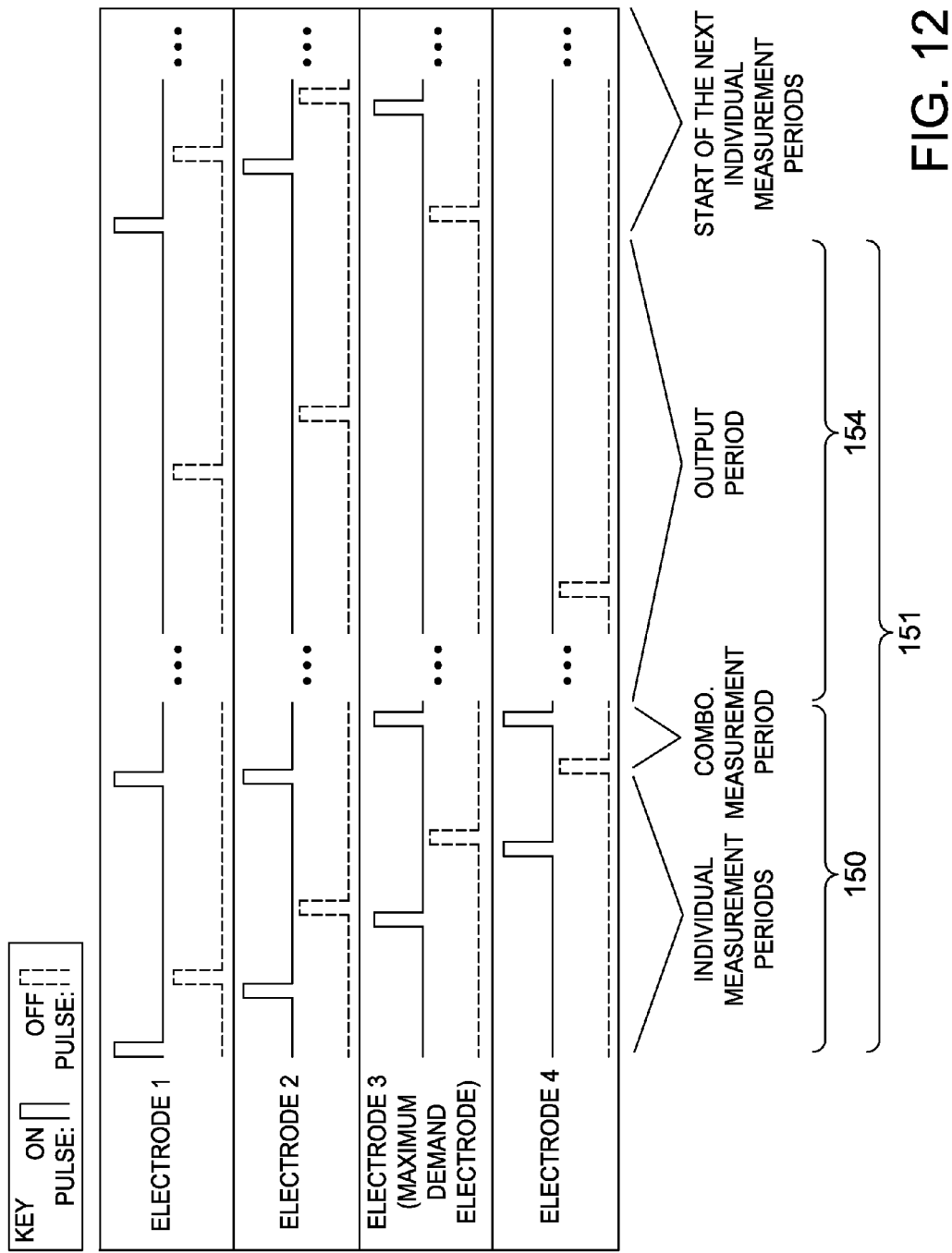
FIG. 12 is a timing diagram of electrode switching signals in the system shown in FIG. 1.

During an output cycle 151, the primary DSP 156 switches electrodes 112 on or off by sending on or off pulses to a pulse transformer (not shown). As shown in FIG. 12, dead time between electrode 112 switching is avoided by switching on the next electrode 112 before the current one is switched off. This eliminates any electrical transient that might otherwise result from this switching.

The length of the output cycle 151 is chosen to substantially minimize the minimum duty cycle while not impacting responsiveness of the control system. If the minimum duty cycle were too large, controller 128 would not be able to deliver power low enough to keep electrodes 112 with very good arterial contact from overshooting the temperature set-point. If the output cycle 151 were too long, the control system would not be able to react quickly enough to changing conditions.

Figure 8:
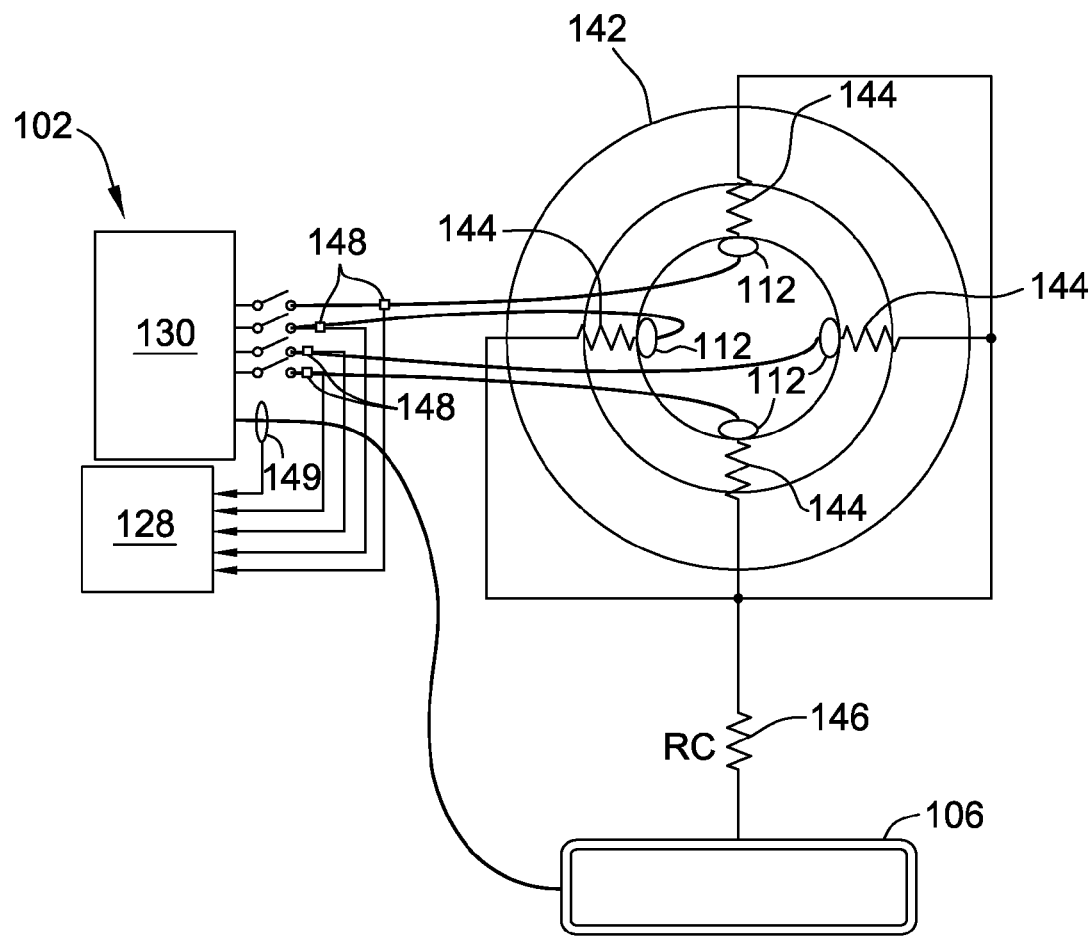
FIG. 8 is an equivalent circuit diagram of the system shown in FIG. 1 when in use within an artery.

As shown in FIG. 8, when the target output voltage is delivered to the electrodes 112 within an artery 142, energy is dissipated in a therapeutic resistance 144 and a common return path resistance 146. Dissipation of energy through the therapeutic resistance 144 results in the local temperature increases in the wall of the artery 142 desired for ablation. Energy dissipated through the common return path resistance 146 does not increase the temperature in the wall of the artery and is thus considered a non-therapeutic dissipation. Accordingly, to accurately determine the energy dissipated in the therapeutic resistance 144, the values of the therapeutic resistances 144 and the common return path resistance 146 need to be determined. The values for the resistances 144 and 146 will change based on location of the electrodes 112 relative to the return electrode 106, the quality of the contact between electrodes 112 and the walls of the artery 142, the temperature of the walls of the artery 142, etc. Therefore, during the measurement period 150 at the beginning of each output cycle 151, controller 128 acquires several measurements to allow it to determine the common return path resistance 146 and the therapeutic resistances 144.

The primary DSP 156 calculates impedance and power for each electrode 112 based on a set of simultaneously sampled voltage-current pairs taken during the measurement period 150 at the beginning of each output cycle 151 using its ADC 172. Root mean square (RMS) voltage and RMS current for each electrode path, i.e., the path from the connected electrode(s) 112 to the return electrode 106, are also calculated. RMS values are needed because the output voltage that is being sampled is not direct current (DC). There is a single current sensor 149 for each DSP 156 and 158 on the return path for all electrodes 112. Therefore, in order to measure the current flowing through a single electrode 112, that electrode 112 must be the only electrode 112 connected to the output during its measurement period.

Because the generator 102 operates with multiple electrodes 112 simultaneously connected to the output, calculating the power dissipated at a specific electrode 112 requires the common return path resistance 146 to be determined and accounted for. To calculate this value, additional voltage and current measurements must be taken with at least two electrodes 112 connected to the output. This measurement period is referred to as the "combo" measurement period. If only one electrode 112 is enabled, the common return path resistance 146 cannot be determined, but accurate computation of power delivered when only a single electrode 112 is enabled does not require such a determination of the common return path resistance 146.

During the measurement period 150 at the beginning of an output cycle 151, voltage and current are measured with each enabled electrode 112 connected to the target output voltage by itself while all other electrodes 112 are disconnected, and with two electrodes 112 connected while all other electrodes 112 are disconnected (i.e., combo measurement period). As graphically shown in FIGS. 9-12, the measurement period 150 of the output cycle 151 is divided into a number of equal length measurement sub-periods 152. In the illustrated embodiment, each measurement sub-period 152 lasts for one hundred and twenty microseconds. The number of measurement sub-periods 152 is determined by the number of electrodes 112 to be enabled. For example, there is one more measurement sub-period 152 than the number of electrodes 112 to be enabled. Accordingly, FIGS. 9 and 11 have five measurement sub-periods 152 with four electrodes 112 enabled, and FIG. 10 has four measurement sub-periods 152 with three electrodes 112 enabled. During each of the measurement sub-periods 152, except the last sub-period 152, a different one of the electrodes 112 is coupled to the target output voltage. Voltage sensors 148 (FIG. 8) are sampled by the controller 128 to measure the voltage across the therapeutic resistance 144 of a particular electrode 112 and the common return path resistance 146. The path from a particular electrode 112 through the common return electrode 106 is sometimes referred to herein as a branch. A current sensor 149 (shown in FIG. 8) is sampled by controller 128 to determine the current through the branch to which the target output voltage is coupled. During the last measurement sub-period 152, two electrodes 112 are coupled to the target output voltage defining a combined branch. The voltage sensors 148 provide the voltage across the combined branch and the current sensor 149 detects the common return path current. In other embodiments, the combined branch may be measured during a sub-period 152 other than the last sub-period 152.

For mitigation purposes, the secondary DSP 158 (shown in FIG. 4) also calculates impedance, average power, etc. for each electrode 112. Besides measuring voltage and current, it must also measure the duty cycle of the power output at each electrode 112, as controlled by the primary DSP 156 (shown in FIG. 4), in order to calculate average power. The HRCAP module 176 (shown in FIG. 5) is used to make this measurement by capturing the times between "on" and "off" pulses generated by the PWM modules 174 on the primary DSP 156. Since there are eight signals being captured and only four capture devices, four set-reset (SR) latches (not shown) are utilized. Each latch is set by an "on" pulse and reset by an "off" pulse, and the HRCAP modules 176 capture the high and low times of the output signals from the latches.

Since the primary DSP 156 controls when the electrodes 112 are connected to the output, a synchronization mechanism is required for the secondary DSP 158 to take voltage and current measurements while electrodes 112 are individually connected to the output. The HRCAP module 176 is used for this functionality as well, with interrupts being generated on rising edges. When the output of a latch connected to an HRCAP module 176 transitions from low to high, it is an indication that the associated electrode 112 has been connected to the output. When such an interrupt occurs, if no interrupts have been generated on the other HRCAP modules 176, the secondary DSP 158 can infer that the particular electrode 112 is individually connected to the output and that it can kick off voltage and current sampling for that electrode.

An issue with using the HRCAP peripheral for measurement synchronization is presented when an electrode 112 has been connected for the maximum duration during an output cycle 151 and is then about to be individually connected for measurements at the start of the next output cycle 151. In this case, the associated SR latch will never be reset, and the HRCAP module 176 will not detect a rising edge to indicate that the electrode 112 is now individually connected. To overcome this, the primary DSP 156 generates a fifth PWM signal which is synchronized with the other PWM modules 174 used for connecting and disconnecting electrodes 112. This fifth signal briefly disables the SR latches once per output cycle, ensuring that the HRCAP modules 176 on the secondary DSP 158 will always detect a rising edge for the first measurement sub-period 152 of an output cycle 151.

As shown in FIGS. 9-12, following completion of the measurement period 150, the output period 154 begins and controller 128 couples the target output voltage to all of the electrodes 112. The controller 128 uses the current measured through each branch during the measurement period 150 and the calculated therapeutic resistance 144 to determine the amount of energy dissipated through each electrode 112 during the measurement period 150 and to determine a remaining amount of energy to be dissipated through each electrode 112. The controller 128 generally keeps each electrode 112 coupled to the target output voltage until the energy dissipated through the electrode 112 during the output cycle 151 reaches the desired energy dissipation determined based on the desired power calculation of the outer loop 178. The last electrode 112 coupled to the target output voltage is maintained coupled to the target output voltage until the end 155 of the output cycle 151. Thus, in the illustrated embodiment with all four electrodes 112 enabled, there are four configurations during the output period 154. In order of occurrence, the configurations are: all four electrodes 112 coupled to the target output voltage, three electrodes 112 coupled to the target output voltage, two electrodes 112 coupled to the target output voltage, and one electrode 112 coupled to the target output voltage. At the beginning of any configuration, the remaining energy to be dissipated through an electrode 112 still coupled to the target output voltage is its desired energy dissipation less the energy dissipated during the measurement period 150 and during any earlier configurations.

The amount of time each electrode 112 is switched on (i.e. electrically coupled to the target output voltage, during the output period 154 of the output cycle 151) is determined by an iterative calculation based on the desired energy dissipation through each electrode 112. Until all electrodes 112 are dropped, the remaining energy to deliver is calculated for each electrode 112 still switched on, (for the initial calculation, energy delivered during the measurement period 150 is also taken into account). Based on the earlier measured output voltage, the common return path resistance 146, and the calculated resistances 144 of the remaining 'on' electrodes 112, updated branch currents are calculated. Based on the updated branch currents and the remaining energy to deliver to each electrode 112, the remaining on time for each electrode 112 is calculated. The on time for the electrode 112 with smallest on time is recorded and that electrode is turned off for the next iteration. Because at least one electrode 112 is switched on at all times and the output cycle is fixed at 5 milliseconds (ms), the electrode 112. This electrode 112 with the largest on time (i.e., the maximum demand electrode) is left on for the entire duration of the output period 154. The difference between this electrode's actual on time and desired on time is used to calculate the energy dissipation difference that is used as feedback for the inner loop 180.

During the output period 154 following the measurement period 150 of the output cycle 151, thermistor and thermocouple measurements are taken. The temperature measurements cannot be taken while the ADC 172 is being used for voltage and current measurements. Temperature measurements take approximately 50 microseconds (μs) each. Thermocouple measurements require a 4 ms delay between switching the thermocouple multiplexer 140 and taking the measurement in order for the signal to settle out. For this reason, only a single thermocouple measurement is taken during an output cycle 151. This means the shortest possible temperature loop 178 (shown in FIG. 7) period is 20 ms, since each temperature is updated once every four cycles. After the thermocouple measurement is completed, the multiplexer 140 (shown in FIG. 3) is switched to the next channel. This results in approximately 5 ms between the multiplexer 140 being switched and the measurement being taken. Due to the thermocouple settle time, the calibration multiplexer channel is only measured while the temperature control loop is inactive. Since any change should occur slowly and should not be severe, using calibration measurements that are taken while the controls are inactive is sufficient. Similar to sampling of the voltages and currents, all temperature ADC sampling is handled by the CLA 166. Once sampling is complete, the processor 136 averages and scales these samples to compute actual temperature values.

After temperature measurements have been taken and the thermocouple multiplexer 140 has been updated, the remainder of the output cycle 151 time is available for control loop computations. The outer loop 178 corresponding to the electrode 112 with the currently updated temperature measurement is run, followed by the voltage loop 180. This yields an effective outer loop period of 20 ms and an inner loop period of 5 ms. While the target output voltage of power supply 126 is set immediately, the newly calculated electrode 'on' times are not put into effect until the next output cycle 151.

During the control loop calculations, the controller 128 uses the measured voltages and currents for each branch, including the combined branch, to determine the value of the therapeutic resistances 144 and the common return path resistance 146. For each electrode 112, controller 128 determines a branch resistance, which is the equivalent resistance of the combination of resistances 144 and 146, by dividing the measured voltage by the measured current for that branch. Controller 128 determines a combined branch resistance for the combined branch by dividing the measured voltage across the combined branch by the measured common return path current for the combined branch. The common return path resistance 146 is determined by $$RC = RX12 - \sqrt{(RX1 - RX12) \cdot (RX2 - RX12)} \quad (1)$$

where RC is the common return path resistance 146, RX12 is the combined branch resistance, RX1 is the branch resistance of the first branch included in the combined branch, and RX2 is the branch resistance of the second branch included in the combined branch. Because each therapeutic resistance 144 is in series with common return path resistance 146 in its respective branch, the therapeutic resistances associated with each electrode may be determined by subtracting the common return path resistance 146 from its determined branch resistance.

As each electrode 112 reaches its desired energy dissipation and is decoupled from the target output voltage, the current through the remaining electrodes 112 and the power dissipated through the associated therapeutic resistances 144 changes. Accordingly, controller 128 calculates the power dissipation in the therapeutic resistances 144 and the remaining energy to be dissipated in the therapeutic resistances 144 for all of the configurations which will occur in the output cycle 151. Controller 128 uses the determined values of therapeutic resistances 144, common return path resistance 146, and the target output voltage to determine the current that will flow through each therapeutic resistance 144 and the power that will be delivered to each therapeutic resistance in each configuration. For each configuration, the amount of energy remaining to be dissipated through each electrode 112 (desired energy less previously delivered energy) is calculated and divided by the power that will be dissipated in the associated therapeutic resistance 144 during that configuration to determine how long the target output voltage would need to be coupled to each electrode 112 at the calculated power to achieve the desired energy dissipation. In each configuration, except the single electrode 112 configuration, the electrode 112 having the least amount of time remaining to reach its desired energy dissipation determines when the configuration ends.

As the output period 154 progresses, the electrodes 112 are decoupled from the target output voltage at the times calculated as described above. For all but the last electrode 112, the desired energy dissipation will have been reached. As described above, however, the last electrode 112 coupled to the target output voltage remains coupled to the target output voltage until the end of the output cycle 151 regardless of whether or not the desired energy for that electrode 112 has been delivered. The difference between the desired energy dissipation for the final electrode and the actual energy dissipation through that electrode is an energy dissipation difference that is used as feedback for the determination of the target output voltage for the next output cycle 151.

Example Timing Calculations

An example illustrating the timing calculations performed by system 100 will now be described. In this example, system 100 includes three enabled electrodes 112 referred to as E1, E2, and E3. The therapeutic resistances 144 associated with E1, E2, and E3 are identified as resistances R1, R2, and R3. RC is the common return path resistance 146. E1 and E2 were simultaneously coupled to the target output voltage during the combination measurement sub-period 152 to form a combination branch. The measured branch currents for E1, E2, and E3 are identified by IX1, IX2, and IX3, respectively. The current through the combination branch during the combination measurement sub-period is IX12. Each measurement sub-period (referred to in this example as 'm') is 2.4% of the output cycle 151 and the output cycle 151 is 0.005 seconds (referred to in this example as 'Tmux'). For simplicity, measured and calculated values are rounded in this example.

The previously determined desired amounts of power to be applied to E1, E2, and E3 are 3.7 watts (W), 4.3 W and 4.1 W, respectively. With an output cycle 151 of 0.005 seconds, the desired energy to be dissipated through R1, R2, and R3 (via E1, E2, and E3 respectively) is 0.019 joules (J) for E1, 0.022 J for E2, and 0.021 J for E3.

During the measurement period 150, the target output voltage applied to E1, E2, and E3 was measured as fifty volts. The branch current IX1 was measured as 0.333 ampere (A), the branch current IX2 was measured as 0.25 A, the branch current IX3 was measured as 0.167 A, and the combination branch current IX12 was measured as 0.41 A.

Branch resistances are calculated for each branch by dividing the measured voltage by the measured branch resistance. Thus, for E1, fifty volts divided by 0.333 A gives a value of 150 ohms ($\Omega$) for the branch resistance RX1. The branch resistances RX2 and RX3 are similarly calculated to be 200$\Omega$ and 300$\Omega$, respectively. Combination resistance RX12 is calculated to be 121.875$\Omega$. The common return path resistance 146 is calculated using:

$$RC = RX12 - \sqrt{(RX1 - RX12) \cdot (RX2 - RX12)} = 75\Omega \quad (2)$$

For each branch, the therapeutic resistance is determined by subtracting RC from the branch resistance. Thus, $$R1 = RX1 - RC = 75\Omega \quad (3)$$

$$R2 = RX2 - RC = 125\Omega \quad (4)$$

$$R3 = RX3 - RC = 225\Omega \quad (5)$$

After the individual resistive elements have been calculated, the controller 128 iteratively calculates the remaining on-times for each electrode 112. The measurement cycle has delivered a portion of the target energy to each load element and that energy must be subtracted from the target energy to compute remaining energy for each electrode 112. The amount of energy remaining to be delivered to R3 through E3 is $$JR3 = J3 - (m \cdot Tmux \cdot IX3^2 \cdot RX3) = 0.0195J \quad (6)$$

where J3 is the previously determined amount of energy to be delivered through E3. Because E1 and E2 were turned on individually and in combination, the calculation of the amount of energy delivered to R1 and R2 must take into account the energy delivered during both the individual measurement and the combination measurement. Accordingly, the remaining energy to be delivered to R1 through E1 is $$JR1 = J1 - (m \cdot Tmux \cdot IX1^2 \cdot RX1) - \left[ m \cdot Tmux \cdot \left[ \frac{v \cdot (IX12 \cdot RC)}{R1} \right]^2 \cdot RX1 \right] = 0.01532 J \quad (7)$$

where J1 is the previously determined amount of energy to be delivered through E1, and v is the measured voltage. The remaining energy to be delivered to R1 through E2 is $$JR2 = J2 - (m \cdot Tmux \cdot IX2^2 \cdot RX2) - \left[ m \cdot Tmux \cdot \left[ \frac{v - (IX12 \cdot RC)}{R2} \right]^2 \cdot RX2 \right] = 0.01943 J \quad (8)$$

where J2 is the previously determined amount of energy to be delivered through E2.

At the beginning of the output period 154, all electrodes 112 are turned on. The time needed to deliver the remaining energy to each electrode 112 in this state ('All-On') is calculated for each electrode 112. The lowest time calculated indicates which electrode 112 to turn off first. Initially, the branch currents need to be calculated for the All-On state. The voltage across RC is calculated as $$VRC = \frac{RC * v}{RC + \left[ \frac{1}{\left(\frac{1}{R1}\right) + \left(\frac{1}{R2}\right) + \left(\frac{1}{R3}\right)} \right]} = 32.955V \quad (9)$$

The current through each resistor is calculated by dividing the voltage across the resistor (v-VRC) by the calculated resistance. This results in a current (I1) of 0.227 A through R1, a current (I2) of 0.136 A through R2, and a current (I3) of 0.076 A through R3. The remaining on times are calculated as $$TR1 = \frac{JR1}{I1 \cdot V} = 1.348 \times 10^{-3} \text{ s} \quad (10)$$

$$TR2 = \frac{JR2}{I2 \cdot V} = 2.85 \times 10^{-3} \text{ s} \quad (11)$$

$$TR3 = \frac{JR3}{I3 \cdot V} = 5.148 \times 10^{-3} \text{ s} \quad (12)$$

where TR1 is the remaining time that E1 must be connected in the current state (All-On) to deliver its targeted energy, TR2 is the remaining time that E2 must be connected in the All-On state to deliver its targeted energy, and TR3 is the remaining time that E2 must be connected in the All-On state to deliver its targeted energy. E1 has the lowest time and will be the first to be switched off. This will occur about 1.35 milliseconds after the measurement period 150 ends, or 1.708 milliseconds into the output cycle, for a duty cycle of about 34.16%. In the controller 128, E1 is turned off and the calculation sequence is repeated for the "Two-On" switch state. Initially, the remaining energy to be delivered is calculated by subtracting the amount of energy delivered during the All-On state from the previously calculated remaining energy. This results in a new JR2 of 0.01024 J and a new JR3 of 0.01439 J. The new voltage across RC is calculated by $$VRC = \frac{RCv}{RC + \left[ \frac{1}{\left(\frac{1}{R2}\right) + \left(\frac{1}{R3}\right)} \right]} = 24.138V \quad (13)$$

The current through each resistor is calculated by dividing the voltage across the resistor (v-VRC) by the calculated resistance. This results in a current (I2) of 0.207 A through R2 and a current (I3) of 0.115 A through R3. The remaining on times are calculated as $$TR2 = \frac{JR2}{I2 \cdot V} = 9.89968 \times 10^{-4} \text{ s} \quad (14)$$

$$TR3 = \frac{JR3}{I3 \cdot V} = 2.50455 \times 10^{-3} \text{ s} \quad (15)$$

E2 now has the lowest time calculated and will be the next output to be switched off. This will occur 990 microseconds after the onset of the 'Two On' switch state, or 2.698 milliseconds into the output cycle for a duty cycle of 53.96%.

The calculation sequence is repeated for the "One-On" state. Although the last electrode 112 will remain on for the entire output period 154, the difference between the calculated time remaining and the time remaining in the output period 154 is used to calculate the energy dissipation difference term for use by the inner control loop 180 to change the output voltage of the power supply 126. The remaining energy to be delivered is calculated by subtracting the amount of energy delivered during the Two-On state from the remaining energy calculated in the last iteration. This results in a new JR3 of 0.00870447 J. The new voltage across RC is calculated by $$VRC = \frac{RCv}{RC = R3} = 12.5V \quad (16)$$

and the current (I3) is calculated as 0.167 A. The remaining on time for E3 is:

$$TR3 = \frac{JR3}{I3 \cdot v} = 1.04454 \times 10^{-3} \text{ s} \quad (17)$$

E3 will hit its output energy target for this output cycle 151 by remaining on for 1.045 milliseconds after the onset of the 'One-On' switch state, or 3.743 milliseconds into the output cycle, for a duty cycle of 74.86%. The output cycle, however is 5 milliseconds in length. The difference between the time when E3 should be turned off to meet its energy target and the end of the output cycle 151 is a difference value of 1.257 milliseconds. This difference value indicates that surplus power was delivered. The difference term is used as an input to the inner voltage loop 180 IIR filter to lower the output voltage of the power supply 126.

Leaving the example and referring now to FIGS. 3-5, in addition to control loop measurements, each DSP 156 and 158 must be able to update watchdog registers in the FPGA 160 before the FPGA 160 generates a system error. The time before an error condition will be generated is approximately 300 ms. While this is a relatively long time period compared to the control loop timings, it is not an insignificant consideration given that communication with the FPGA 160 is accomplished using CAN communications.

Each DSP 156 or 158 also needs to communicate mitigation data to the other DSP 158 or 156. The data being exchanged must be agreed upon by both DSPs 156 and 158. This data includes measurement data (e.g., temperature) and state data (e.g., Ready or Diagnostic state). If there is disagreement or a lack of communication for approximately 100 ms, at least one of the DSPs 156 or 158 will generate a system error. A CAN message will be sent to the FPGA 160 to discontinue output, and CAN messages will be sent to the UI processor 162 and to the other DSP 158 or 156 indicating the error. Mitigation data is exchanged using the McBSP peripheral every 10 ms.

To limit the potential consequences of critical component failure, the secondary DSP 158 monitors the activities of the primary DSP 156. The FPGA 160 is also designed to cut off all power if it does not receive heartbeat packets within a certain timeframe from either DSP 156 or 158.

To mitigate the possibility of a program malfunction due to erroneous memory or bus operation, the memory components attached to the system are checked both at boot time and during normal operation. The flash memory 138 is verified by computing a cyclic redundancy check (CRC) over its contents and comparing it to a previously stored value. RAM tests typically consist of three sections. One section tests the memory 138 itself, and the other two test the data and address bus connections. Since the RAM in this implementation is on-chip, the bus tests are not required; if the buses are not operational, the chip will not function. The RAM test is executed once at system boot and continuously thereafter, running in the lowest-priority task. The check itself consists of reading a memory location, storing its bitwise inverse at the same location, re-reading the result, computing the bitwise exclusive-OR with the original value and ensuring the result is bitwise all ones before restoring the original value. This ensures that all the bits in the memory location can correctly store both ones and zeros. Interrupts must be disabled immediately prior to the first read of the value and re-enabled directly after restoring the original value. Furthermore, it is important to maintain the global state of the interrupt enable/disable register, to avoid inadvertently re-enabling interrupts after another routine has disabled them. Because the processor 136 has an 8-stage pipeline, a flush operation is required before interrupts are re-enabled after a memory test to prevent premature reads from returning corrupted values.

The correct function of the control loop regulating the operating parameters of the catheter 104 (output power and temperature) depend on three issues: the quality of the connection of the analog components to the input of the ADCs 172, the correct operation of the ADCs 172 themselves, and valid outputs to the control loop calculation. The secondary DSP 158, therefore, verifies both the connection of the analog components and the ADC 172 values of the primary DSP 156 by measuring the output current, voltage, and temperature of each electrode 112 via independent analog connections and its own ADCs 172. The sensor values read by the ADC 172 of the primary DSP 156 are compared to the values read by the ADC 172 of the secondary DSP 158, and vice versa. Periodically, both DSPs 156 and 158 exchange their conversion results and verify that the values agree.

Because the connection to each sensor (temperature, voltage, or current) is independent, but the sensor itself is shared between the two DSPs 156 and 158, it is possible to detect a failing sensor by checking whether or not the ADCs 172 of both DSPs 156 and 158 are reading values that are out of range. A poor connection between a DSP 156 or 158 and one of its sensors, or a faulty ADC 172 may be detected when differing values for the same sensor are found on either DSP 172.

The output of the control loop calculation is verified to be within defined limits by the secondary DSP 158 using calculated values from the control loop of the primary DSP 156. The secondary DSP 158 will only issue an alert and abort ablation if the calculated values are out of range for longer than a certain period of time, to prevent frequent aborted ablation sessions due to brief transients that are of no consequence.

Confirmation of the correct operation of all three processing components, i.e., the FPGA 160 and the DSPs 156 and 158, of the system 100 is established by the periodic transmission of RPC watchdog packets from one node to the other two. A certain level of confidence is attained by the reception of periodic status messages by both DSPs 156 and 158 from the FPGA 160, but this does not confirm the normal operation of RPC packet reception by the FPGA 160. For this reason, both DSPs 156 and 158 periodically transmit RPC watchdog packets to the FPGA 160. A similar argument applies to the verification of operation of the primary DSP 156 by the secondary DSP 158. Accordingly, RPC watchdog messages from the secondary DSP 158 to the primary DSP 156 (and vice versa) guarantee prompt detection of problems in either component.

The frequency of the RF energy emitted is important to the ablation procedure. For this reason the secondary DSP 158 decomposes the output waveform into its constituent frequencies via fast Fourier transform (FFT). This permits verification of the correct frequency setting as well as the output waveform, to avoid the emission of unwanted higher frequency sidebands.

In some embodiments, the determined common return path resistance 146 (shown in FIG. 8) is also utilized by the controller 128 for additional features of the ablation system 100. As described above, the ablation system 100 (shown in FIG. 1) includes a single return electrode 106 that is shared with all of the electrodes 112 resulting in a common return path for all of the electrodes 112. Energy dissipated in the common return path resistance 146 does not increase temperatures close to electrodes 112 and does not aid ablation. The larger the common return path resistance 146, the more energy is wasted in nontherapeutic dissipation. Accordingly, in some embodiments, controller 128 generates a notification when the common return path resistance exceeds a threshold value, thereby alerting the operator that the common return path resistance 146 is too high. The operator may attempt to reposition the return electrode 106 to reduce the common return path resistance 146. Alternatively, or additionally, the operator may connect a second return electrode (not shown) to generator 102 to reduce the common return path resistance 146. The notification may be an audible or visual notification, such as by using one or more of indicators 120. In some embodiments, the notification is a unitless visual notification. For example, the notification may be a green light if the common return path resistance 146 is equal to or below the threshold value and a red light if the common return path resistance 146 exceeds the threshold value. Additional threshold values and notifications may be added to increase the resolution of the notification. In some embodiments, the controller 128 is configured to disable the electrodes 112, i.e. decouple the electrodes 112 from the target output voltage and prevent re-coupling to the output voltage, when the common return path resistance 146 exceeds the threshold. In other embodiments, the controller 128 is configured to disable the electrodes 112, when the common return path resistance 146 exceeds a second threshold greater than the first threshold. Thus, the controller 128 may alert the operator when the common return path resistance 146 exceeds a first threshold value and disable the electrodes 112 if the common return path resistance 146 continues to increase above a second threshold value.

Because the controller 128 determines the common return path resistance 146 and the therapeutic resistances 144, the controller 128 is able to accurately determine the power applied to the therapeutic resistances 144. In some embodiments, by combining the accurate power measurements with the temperature measurements for each electrode 112, controller 128 determines the thermal gain for each electrode 112. The thermal gain of an electrode 112 is a change in temperature produced by an amount of power. In the present disclosure, thermal gain is generally the ratio of a change in temperature measured at an electrode 112 (degrees Celsius) to the amount of power applied to that electrode (in watts). The thermal gain of an electrode 112 may change depending on, for example, the size of the electrode 112, the material composition of the electrode 112, the size of an artery in which the electrode 112 is located, the amount of fluid surrounding the electrode 112, the thermal transfer characteristics of the environment around the electrode, and the quality of contact between the electrode and the wall of artery 142. For a particular electrode 112 in a particular artery, a higher thermal gain generally indicates better apposition, or contact, with the wall of the artery than a lower thermal gain. Thus, controller 128 is configured to utilize the thermal gain of the electrodes 112 as an indication of the quality of contact between electrodes 112 and the artery wall. The controller 128 generates a notification corresponding to the thermal gain, and thus the contact quality, for each electrode 112. The notification may be an audible or visual notification, such as by using one or more of indicators 120. In some embodiments, the notification is a unitless visual notification. For example, the notification may be a green light if the contact quality is good and a red light if the contact quality is poor. Additional threshold values and notifications may be added to increase the resolution of the notification. For example, a numerical scale, e.g. integers one through ten, may be displayed to the operator with one end of the scale representing very good contact quality and the opposite end indicating very poor contact quality. Numbers between the ends indicate graduation in quality between very good and very poor. In some embodiments, the controller 128 is configured to disable the electrodes 112, i.e. decouple the electrodes 112 from the target output voltage and prevent re-coupling to the output voltage, when the thermal gain is less than a threshold thermal gain.

In one particular embodiment, the controller 218 is configured to limit a maximum power applied to the electrodes 112 based at least in part on the determined thermal gain of each electrode 112 (sometimes referred to herein as adaptive power limiting). During operation, the maximum power delivered to each electrode is generally limited by a predetermined power limit. In one example, the power limit is eight watts. In other embodiments, however, the power limit may be other than eight watts (higher or lower). The determined thermal gain of each electrode 112 is compared to a predetermined thermal gain threshold that generally indicates adequate contact quality. The thermal gain threshold is twenty degrees Celsius per watt (20° C./W). The exemplary thermal gain threshold of twenty degrees Celsius per watt (20° C./W) was determined based on animal study data for nominal renal artery sizes of five millimeters to six millimeters. Other artery sizes and/or other factors may dictate use of a different thermal gain threshold (whether larger or smaller). In another embodiment, the thermal gain threshold is about fifteen degrees Celsius per watt (15° C./W). In other embodiments, the thermal gain threshold may be any suitable threshold value determined to indicate a minimum arterial contact for an ablation procedure using a particular ablation system. Each electrode 112 that has a thermal gain above the threshold is controlled as described herein subject to the predetermined power limit. Any electrodes for which the thermal gain is less than the thermal gain threshold are limited to a reduced power limit until the thermal gain for that electrode 112 reaches the thermal gain threshold.

The controller 218 determines the reduced power limit, for electrodes 112 having a thermal gain less than the threshold thermal gain, as a function of the amount by which the thermal gain of the electrode 112 is less than the thermal gain threshold. In a more particular embodiment, the reduced power limit is calculated by:

$$P\text{limit}=\text{Max}P\text{limit}-\text{ScalingFactor}*(\text{Threshold}-\text{ThermalGain}) \quad (18)$$

where Plimit is the reduced power limit, MaxPlimit is the original (maximum) power limit, ScalingFactor is a scaling factor, Threshold is the thermal gain threshold, and ThermalGain is the determined thermal gain. The scaling factor in one exemplary embodiment is 0.5. In such an embodiment, the controller 218 reduces the power limit by one half of a watt for each degree Celsius per watt that the determined thermal gain is below the thermal gain threshold. In another exemplary embodiment, the scaling factor may be 0.3. It is understood that in other embodiments the scaling factor may be other than as set forth above without departing from the scope of this disclosure.

The adaptive power limiting is not applied at the beginning of an ablation procedure in order to permit the thermal gain values to reach equilibrium as the electrode temperature ramps up to the temperature set-point. Rather, in one embodiment, the adaptive power limit feature is activated upon the occurrence of a suitable startup condition. The startup condition may be, for example, the first to occur of the electrode temperature reaching a temperature threshold or the energy dissipated through the electrode reaching an energy threshold. In one exemplary embodiment, the temperature threshold is sixty-five degrees Celsius (65° C.) and the energy threshold is twelve joules (12 J). Alternatively, the temperature threshold and/or the energy threshold may be any other suitable respective threshold. For each electrode 112, after at least one of the startup conditions has been met, the adaptive power limit described above is applied to that electrode as applicable.

Figure 24:
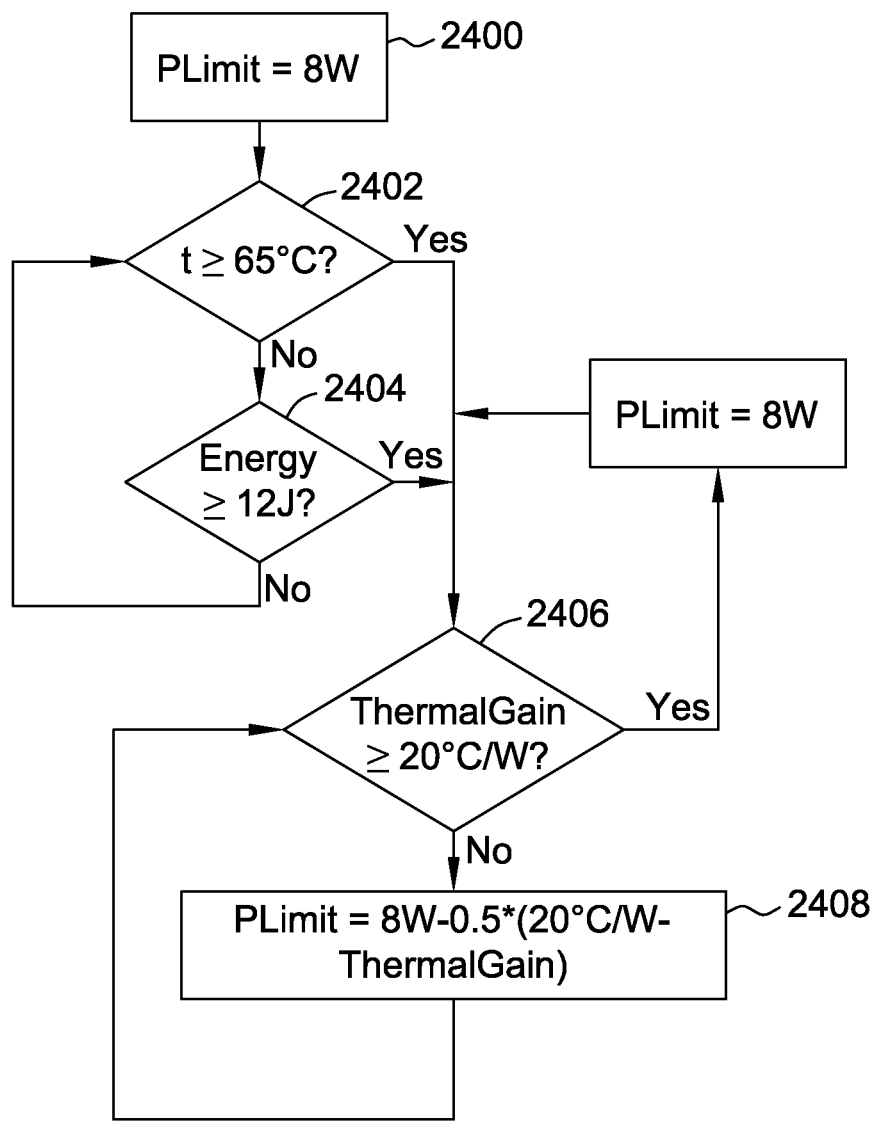
FIG. 24 is a flow diagram of an implementation of adaptive power limiting in an ablation system.

FIG. 24 is a flow diagram of one exemplary implementation of adaptive power limiting in the ablation system 100. For this example, the maximum power limit is eight watts, the thermal gain threshold is twenty degrees Celsius per watt (20° C./W), the scaling factor is 0.5, and the startup condition is the first to occur of the electrode temperature reaching a startup temperature threshold or the energy dissipated through the electrode reaching a startup energy threshold. An ablation procedure begins at step 2400 and the power limit (PLimit) is set to eight watts. At 2402, the controller 218 determines whether or not the temperature (t) at an electrode 112 is greater than or equal to the startup temperature threshold of sixty-five degrees Celsius (65° C.). If not, the controller determines at 2404 whether or not the energy dissipated through the electrode 112 equals or exceeds the startup energy threshold of twelve joules (12 J). If not, the controller 218 returns to 2402. If the temperature exceeds the startup temperature threshold at 2402 or the energy exceeds the startup energy threshold at 2404, the controller proceeds to step 2406. As long as the determined thermal gain (ThermalGain) for the electrode 112 equals or exceeds the threshold thermal gain of twenty degrees Celsius per watt (20° C./W), the power limit remains at the original setting (i.e., eight watts). If the determined thermal gain is less than the threshold thermal gain, the power limit is reduced according to equation (18) at step 2408. Moreover, throughout the ablation procedure, the determined thermal gain may be communicated to the operator of the ablation system 100 as described above.

FIGS. 15A, 15B, and 15C and FIGS. 16A, 16B, and 16C graphically illustrate computer simulations of a portion of a single sixty second long ablation procedure using the adaptive power limiting described herein. FIGS. 15A, 15B, and 15C are the graphical results of a simulated ablation procedure without use of the adaptive power limiting, while FIGS. 16A, 16B, and 16C are the graphical results of a simulated ablation procedure using the adaptive power limiting. For both of these examples, the maximum power limit is eight watts. Beginning at about five seconds into the ablation procedure, the temperature set-point ramps up from the ambient temperature (about forty degrees Celsius, 40° C.) to the ablation set-point of seventy degrees Celsius (70° C.). Contact between the electrode 112 and the artery wall decreases sharply about twenty seconds into the ablation procedure. These simulations approximate an arterial spasm decreasing contact of the electrode 112 with the artery wall for about five seconds.

In particular, FIG. 15A presents the electrode temperature set-point 1500 and the measured electrode temperature 1502. FIG. 15B shows the power 1504 delivered to the electrode 112, and FIG. 15C is a graph of the thermal gain 1506 of the electrode 112. At approximately twenty seconds, the thermal gain 1506 drops rapidly from forty degrees Celsius per watt (40° C./W) to five degrees Celsius per watt (5° C./W) and the temperature 1502 decreases below the temperature set-point 1500. The controller 218 attempts to increase the electrode temperature 1502 back to the set-point 1500 by supplying additional power 1504 to the electrode 112. Because of the decreased arterial contact (and accordingly decreased thermal gain 1506), the additional power is unable to increase the temperature 1502 back to the set-point 1500. The power 1504 applied to the electrode 112 thus increases, without significantly increasing the temperature 1502, until the eight watt power limit is reached at about twenty-two seconds. When the thermal gain returns to forty degrees Celsius per watt (40° C./W) at about twenty-five seconds, the electrode temperature 1502 spikes up above the temperature set-point due to the large amount of power being applied to the electrode 112.

Turning now to the simulation illustrated by FIGS. 16A, 16B, and 16C including the adaptive power limiting, FIG. 16A presents the temperature set-point 1600 and the electrode temperature 1602. FIG. 16B shows the power 1604 delivered to the electrode 112 and the power limit 1605. FIG. 16C graphs the actual thermal gain 1606 of the electrode 112 and the determined thermal gain 1608. At approximately twenty seconds, the actual thermal gain 1606 drops rapidly from 40° C./W to 5° C./W and the temperature 1602 decreases below the temperature set-point 1600. The determined thermal gain 1608 decreases slower than the actual thermal gain 1606. While the determined thermal gain 1608 remains above a thermal gain threshold of 20° C./W, the controller 218 attempts to increase the electrode temperature 1602 back to the set-point 1600 by supplying additional power 1604 to the electrode 112. Because of the decreased arterial contact (and accordingly decreased thermal gain 1606), the additional power is unable to increase the temperature 1602 back to the set-point 1600. Once the determined thermal gain decreases below 20° C./W, the controller 218 decreases the power limit 1605 proportional to the difference between the determined thermal gain 1608 and the threshold. The power 1604 applied to the electrode 112 is limited to the reduced power limit 1605, and the electrode temperature 1602 continues to decrease. When the actual thermal gain returns to 40° C./W at about twenty-five seconds, the electrode temperature 1602 and the determined thermal gain 1608 begin to increase gradually. As the determined thermal gain 1608 increases, the reduced power limit 1605 increases. Once the determined thermal gain 1608 is above the 20° C./W threshold, the power limit 1605 has returned to the original eight watts. As can be seen, the adaptive power limiting inhibits a spike in the electrode temperature 1602 above the temperature set-point 1600, as well as inhibiting application of significant power to the electrode 112 when it is not in good contact with the artery wall.

Figure 17:
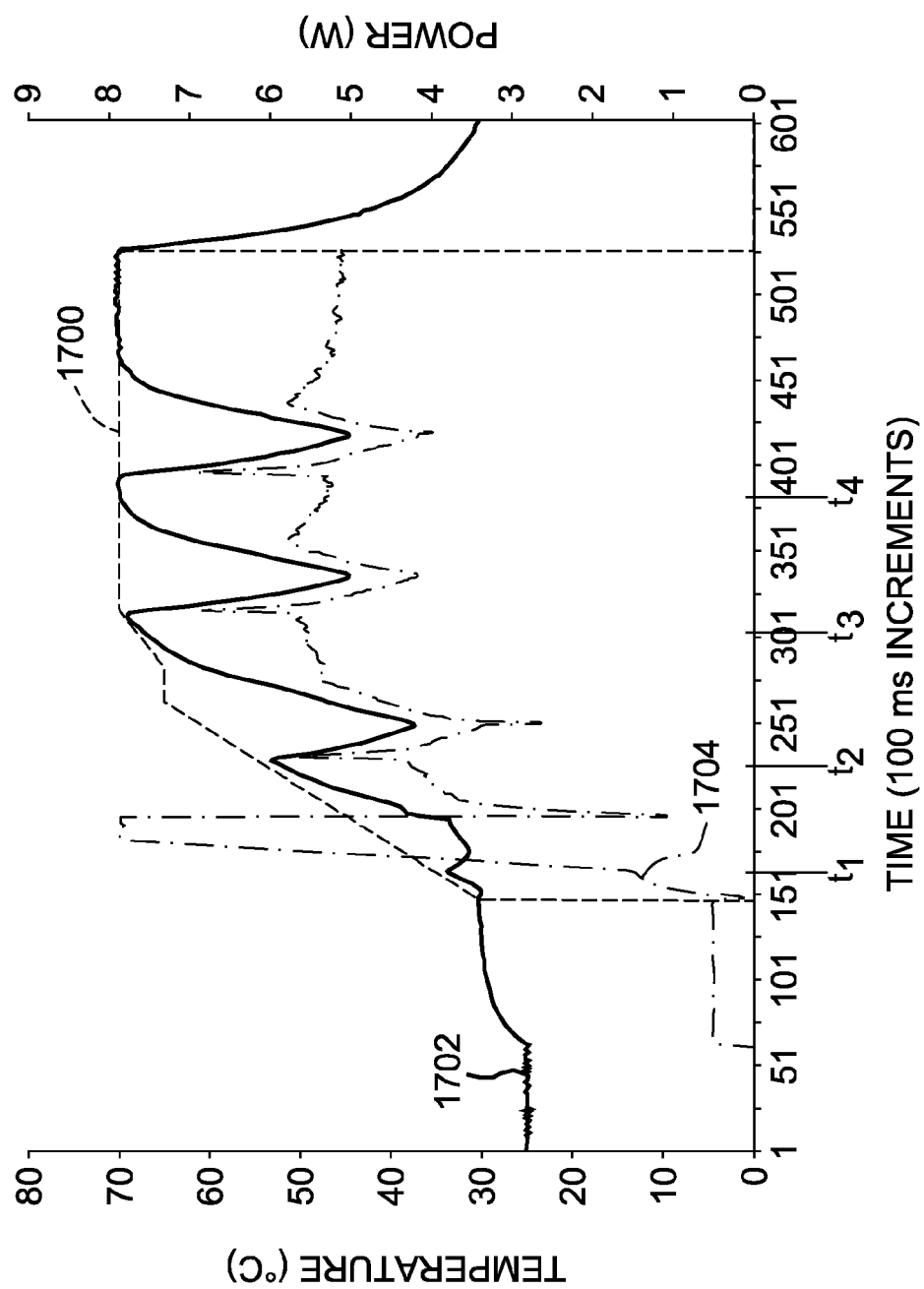
FIG. 17 is a graph of electrode temperature, temperature set-point, and power delivered to the electrode during a bench simulated ablation.

FIG. 17 is a graphical presentation of the results of a bench-top test of a single sixty second ablation procedure using the ablation system 100 including the adaptive power limiting described herein. FIG. 17 presents the temperature set-point 1700, the electrode temperature 1702, and the electrode power 1704 versus time. The time scale is in one hundred millisecond (100 ms) increments. The maximum power limit in this test is eight watts and the startup conditions are an electrode temperature of sixty-five degrees Celsius (65° C.) or twelve joules (12 J) of energy delivered. At about fifteen seconds into the procedure, the temperature set-point begins to ramp up from ambient temperature to seventy degrees Celsius (70° C.). Four spasms, which cause the thermal gain to drop rapidly, are simulated at times t1, t2, t3, and t4. During the first spasm, neither startup condition has been met and the adaptive power limiting is not applied. The power 1704 increases rapidly until the power limit of eight watts is reached. The startup condition is met before the second, third and fourth simulated spasms. As can be seen, the reduced power limit is applied to prevent the power 1704 from increasing during the spasms and preventing the temperature 1702 from spiking up following the spasms.

Figure 18:
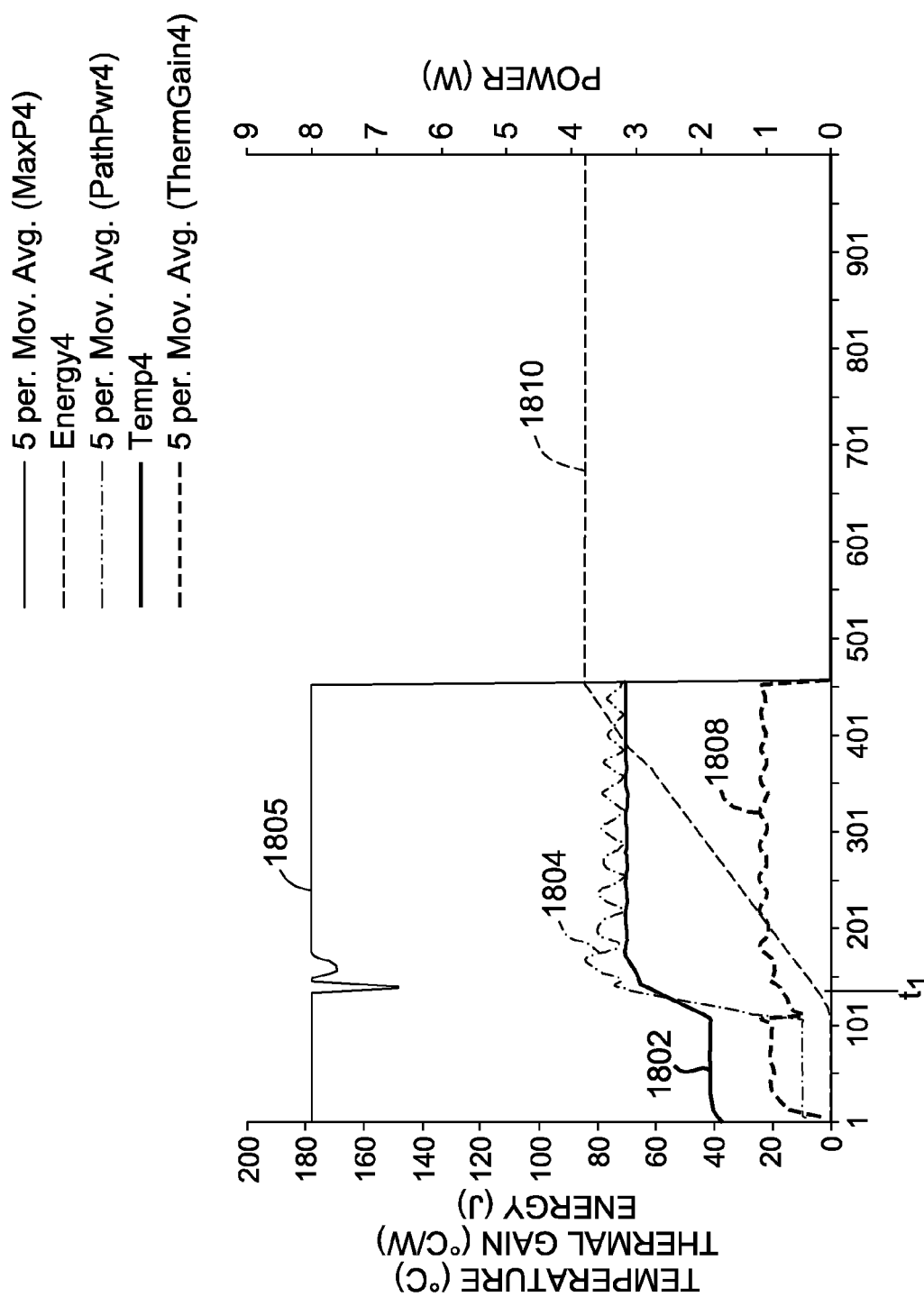
FIG. 18 is a graph of electrode temperature, thermal gain, power limit, power delivered to the electrode, and energy dissipated through the electrode during an animal ablation test.
Figure 19:
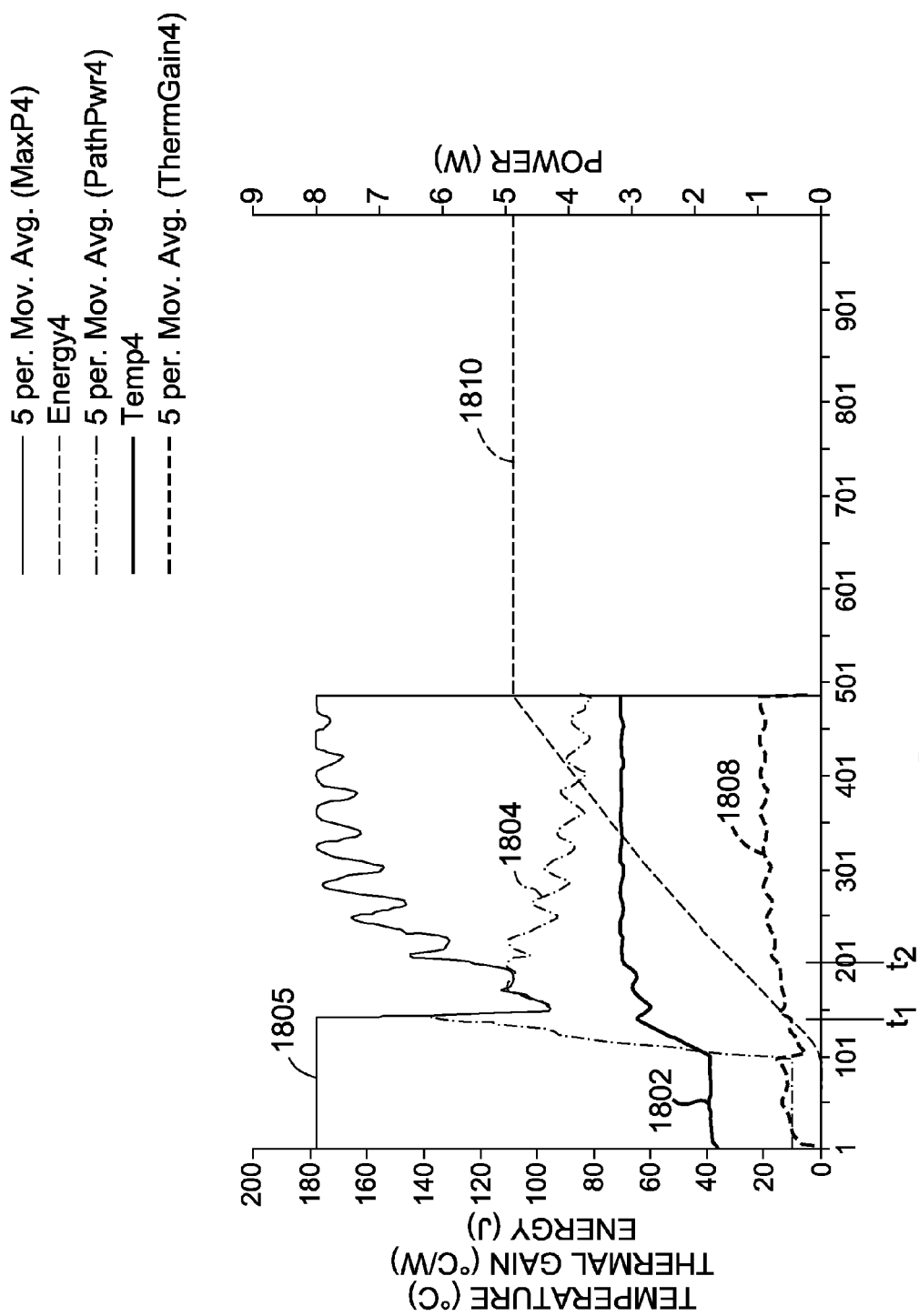
FIG. 19 is a graph of electrode temperature, thermal gain, power limit, power delivered to the electrode, and energy dissipated through the electrode during another animal ablation test.
Figure 20:
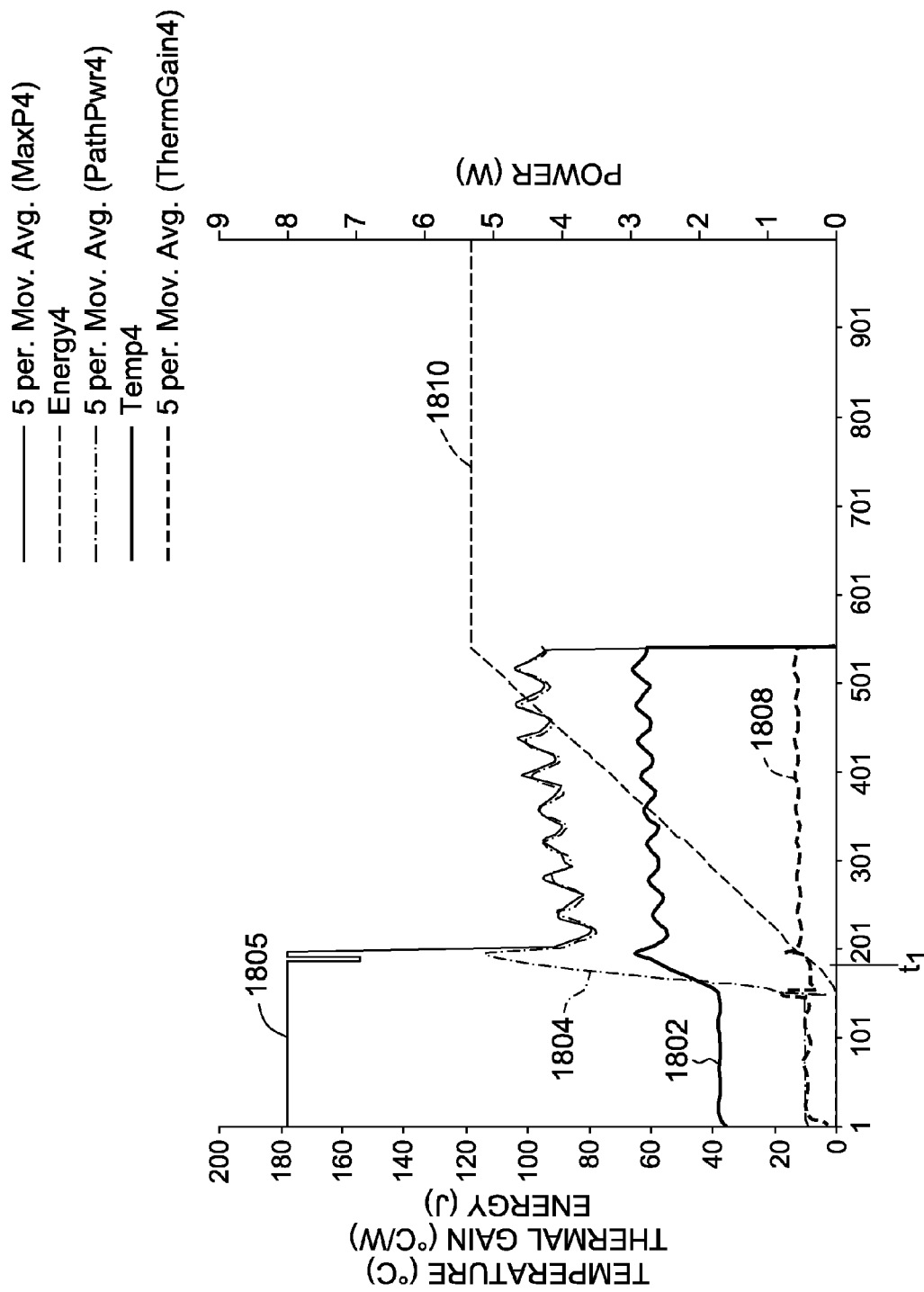
FIG. 20 is a graph of electrode temperature, thermal gain, power limit, power delivered to the electrode, and energy dissipated through the electrode during an animal ablation test.

FIGS. 18-20 graphically present the results of three separate sixty second ablation procedure animal tests of the system 100 with the adaptive power limiting. Each figure represents the measurements of a single electrode 112 during a different test. The time scale is in one hundred millisecond (100 ms) increments. The maximum power limit in this test is eight watts and the startup conditions are an electrode temperature of sixty-five degrees Celsius (65° C.) or twelve joules (12 J) of energy delivered. The thermal gain threshold is twenty degrees Celsius per watt (20° C./W), and the electrode temperature set-point (not shown) begins to ramp up to seventy degrees Celsius (70° C.) at about ten seconds into the procedure. All three figures present the electrode temperature 1802, the electrode power 1804, the power limit 1805, the thermal gain 1808 of the electrode 112, and the energy 1810 dissipated through the electrode 112 as a function of time.

In FIG. 18, the startup condition is met and the adaptive power limit is activated at about time t1. At time t1, the thermal gain 1808 is slightly less than the threshold thermal gain of 20° C./W and the power limit 1805 decreases, but the thermal gain 1808 returns above 20° C./W before the power limit 1805 decreases enough to impact operation of the ablation system 100. Throughout the ablation procedure shown in FIG. 18, the temperature 1802 remains fairly constant at the temperature set-point of seventy degrees Celsius (70° C.) after it is ramped up to that temperature.

In FIG. 19, the startup condition is met and the adaptive power limit is activated at about time t1. At time t1, the thermal gain 1808 is less than the threshold thermal gain of 20° C./W and the power limit 1805 decreases. The power 1804 delivered to the electrode 112 is limited to the reduced power limit 1805. As the thermal gain 1808 varies after time t1, the power limit 1805 is correspondingly varied. After about time t2, the thermal gain, although varying, remains close to the threshold 20° C./W and the power limit 1805 remains close to the maximum power limit of eight watts. Throughout the ablation procedure shown in FIG. 19, the temperature 1802 remains fairly constant at the temperature set-point of seventy degrees Celsius (70° C.) after about time t2.

In FIG. 20, the startup condition is met and the adaptive power limit is activated at about time t1. In this test, there is poor contact between the electrode 112 and the artery wall. At time t1, the thermal gain 1808 is less than the threshold thermal gain of 20° C./W and the power limit 1805 decreases. The power 1804 delivered to the electrode 112 is limited to the reduced power limit 1805. As the thermal gain 1808 varies after time t1, the power limit 1805 is correspondingly varied. After time t1, the thermal gain 1808 remains well below the threshold 20° C./W and the power limit 1805 remains relatively low (around four watts) and limits the power applied to the electrode 112 for the remainder of the period of the ablation procedure. In this test, the temperature 1802 is limited by the low thermal gain 1808 and the power limit 1805, fluctuating between about fifty-five and sixty-five degrees Celsius (55° C.-65° C.) after time t1.

Figure 21:
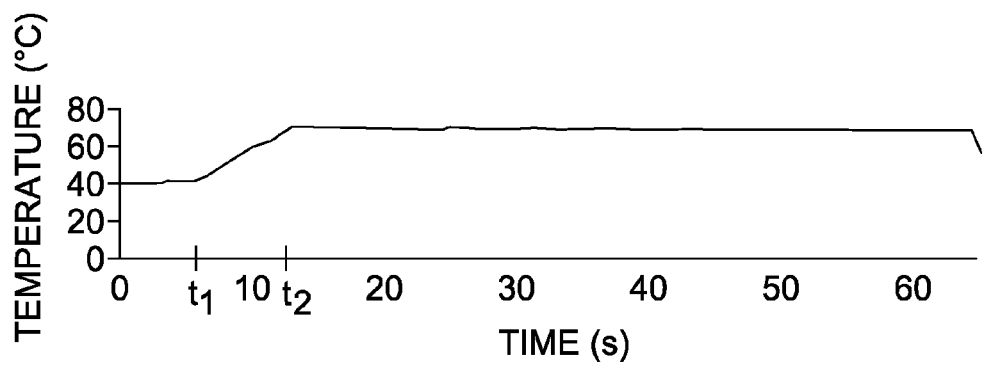
FIG. 21 is graph of an electrode temperature during a simulated ablation.
Figure 22:
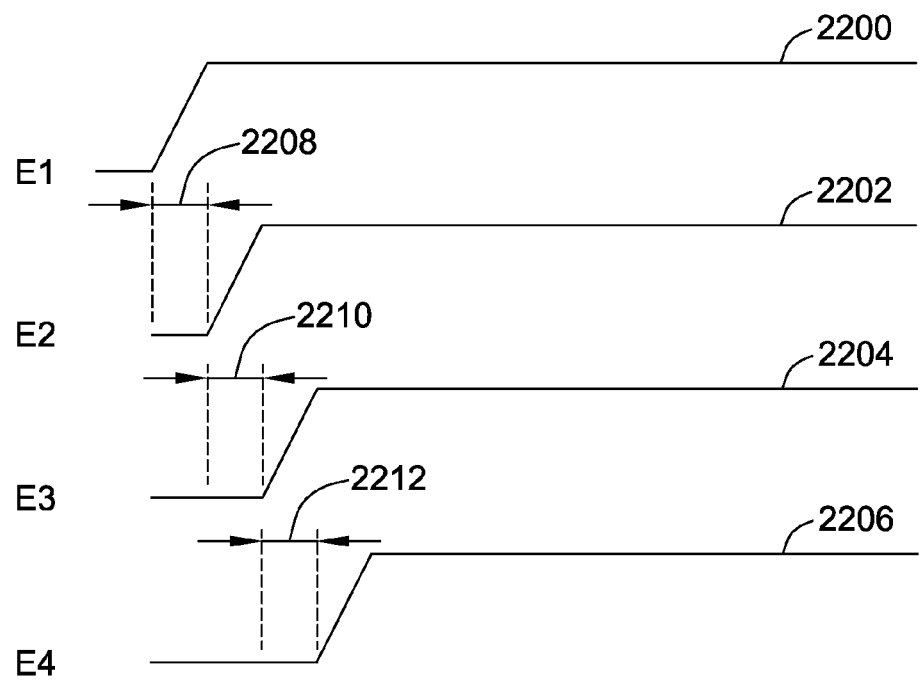
FIG. 22 is graph of electrode temperature for four electrodes during a simulated ablation.
Figure 23:
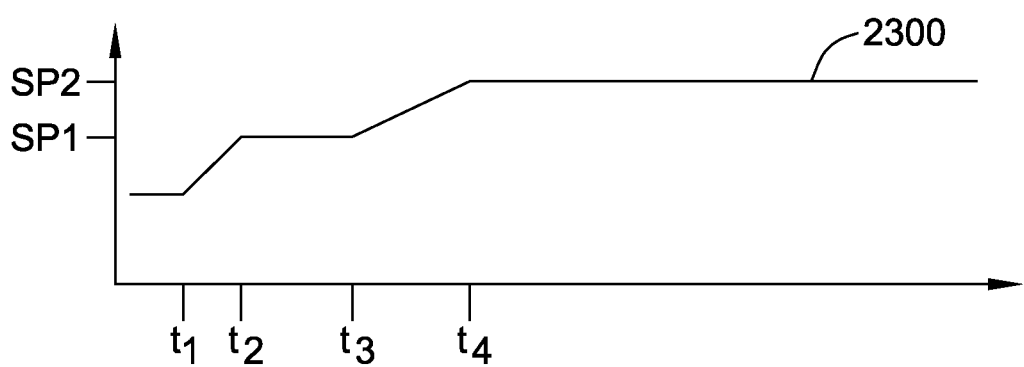
FIG. 23 is graph of electrode temperature with a two stage ramp during a simulated ablation.

With reference now to FIGS. 21-23, at the beginning of an ablation procedure, the system 100 (and more specifically the controller 218) gradually increases the temperature at each electrode 112 until the temperature reaches a temperature set-point. Ramping up the temperature at the electrodes 112 allows lesion formation and desensitizes the artery at a lower temperature before the full ablation temperature is reached, which may reduce arterial spasms. FIG. 21 shows the temperature 2100 of one electrode 112 for a sixty second ablation procedure. The temperature 2100 begins at about forty degrees Celsius (40° C., i.e., around body temperature). At time t1, controller 218 selectively couples the electrode 112 to the generator output to increase the temperature 2100 at a predetermined rate (in degrees Celsius per second) of increase. At time t2, the temperature 2100 has reached the temperature set-point of seventy degrees Celsius (70° C.) and controller 218 selectively couples the electrode 112 to the generator output to maintain the temperature 2100 at the temperature set-point. The predetermined rate of increase applied to each electrode 112 may be the same or different.

Moreover, the beginning of the temperature increase for each electrode 112 may occur concurrently, or at different times. For example, FIG. 22 shows the temperatures 2200, 2202, 2204, and 2206 of four electrodes E1, E2, E3, and E4 (collectively referred to as electrodes 112). The beginning of the temperature increase for each electrode 112 is staggered by a delay period. Thus, the temperature 2202 on electrode E2 begins to increase after the delay period 2208 following the beginning of the increase of the temperature 2204 on electrode E1. Similarly, the temperature 2204 of electrode E3 begins to increase following the delay period 2210 and the temperature 2206 on electrode E4 begins its increase after the delay period 2212.

In some embodiments, the temperature of the electrodes 112 is increased in more than one stage. FIG. 23 graphically presents an example of a two stage ramp up of the electrode temperature 2300 for an electrode 112. It is also understood that more than two stages may be used. At time t1, the controller 218 begins to increase the temperature of the electrode 112 at a first predetermined rate. When the temperature 2300 reaches a first temperature set-point SP1, the controller 218 selectively couples the electrode 112 to the generator to maintain the temperature at the set-point SP1 for a dwell period (from time t2 to time t3). Following the dwell period, the controller 218 selectively couples the electrode 112 to the generator to increase the temperature 2300 at a second predetermined rate to a second temperature set-point SP2. The controller 218 then maintains the temperature 2300 at the second temperature set-point SP2 for the remainder of the ablation procedure. The second predetermined rate is not the same as the first predetermined rate. Specifically, the second predetermined rate is slower than the first predetermined rate (i.e., fewer degrees Celsius per second). In an exemplary embodiment, the first rate is four degrees Celsius per second (4° C./second), the first temperature set-point is sixty five degrees Celsius (65° C.), the second rate is one degree Celsius per second (1° C./second), and the second temperature set-point is seventy degrees Celsius (70° C.). In other embodiments, any other suitable rate may be used for the first and second rates, including the same rate. Moreover, in some embodiments, the dwell period is omitted (or has a value of zero seconds).

At various times during operation, the controller 128 samples the output voltage of the generator 102. The output voltage of the generator 102 is the output of the RF output circuit 130 and is a generally sinusoidal, time invariant output signal having a known output frequency. In the illustrated embodiment, the output signal has a frequency of 480 kilohertz (kHz). The illustrated controller 128 is capable of sampling the output signal at a rate of 1.6 megsamples per second (MS/s). Accordingly, the controller 128 is able to acquire approximately three samples of the output signal during one period of the output cycle. To improve the resolution of the sampling of the output voltage, the controller 128 samples the output voltage at different phases throughout many periods of the output signal and combines the multi-period samples into a representation of a single period of the output signal.

In general, the sampling method employed by the controller 128 involves sampling a time invariant output signal at a sampling rate that results in the samples of the output signal in any period of the output signal being acquired at different phases of the output signal than the samples acquired during the immediately previous period. The shift in the phase of the samples is fixed by the frequency of the output signal and the sample rate. Specifically, the sample shift in time is defined by:

$$\text{sample shift} = (n * \text{sample period}) - \text{output period} \quad (19)$$

where the sample period is the period of the sampling, the output period is the period of the output signal, and n is the smallest integer value that results in a sample shift greater than zero. In order for the sampling method described herein to be used, the sample shift cannot equal zero. In other words the output period cannot be evenly divisible by the sample period. If the sample shift equals zero, the output period or the sample period can be adjusted to produce a nonzero sample shift. The amount of the phase shift may be found by:

$$\text{phase shift} = \frac{\text{sample shift}}{\text{output period}} * 360° \quad (20)$$

Because the frequency of the output signal and the sampling rate are fixed, the phase shift will advance the phase of the samples throughout a number of periods until the samples during a period of the output signal substantially align with the phases sampled in the first period sampled. The number of samples (S) that are acquired before this occurs is the smallest integer S that satisfies:

$$\text{remainder of } \left(S * \frac{\text{phase shift}}{360°}\right) = 0 \quad (21)$$

The number of output signal periods that are sampled before the sample phases realign with the first period sample phases, sometimes referred to herein as a superperiod, may be found by dividing the number of samples by the number of samples that may be acquired in one period of the output signal, i.e. n−1 samples. The resolution of the sampling is:

$$\text{resolution} = \frac{S}{360°} \quad (22)$$

The samples acquired during such a superperiod are combined as a function of phase to produce a representation of a single period of the output signal.

Sampling Example

Figure 13:
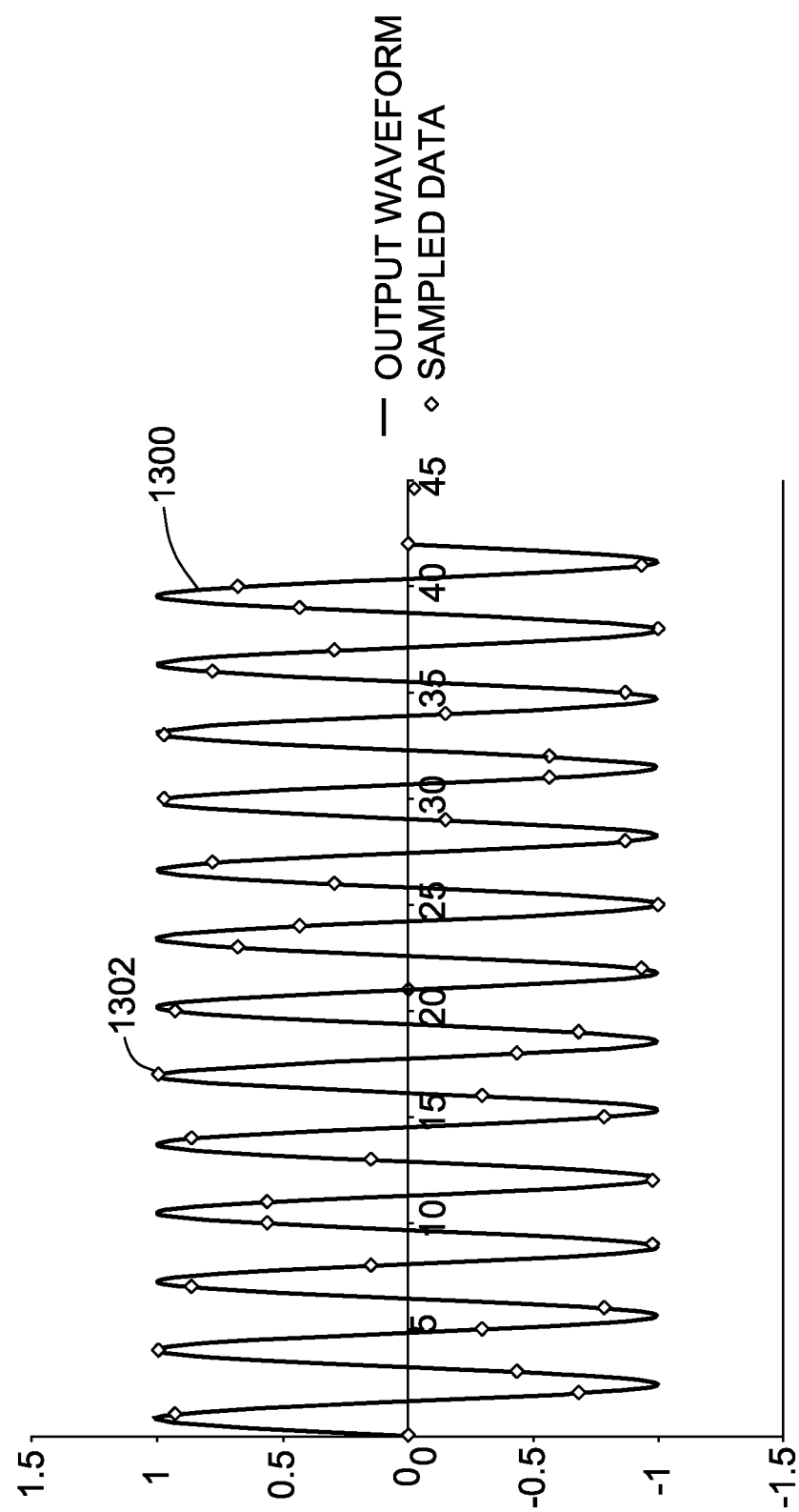
FIG. 13 is a graphical representation of an output signal waveform from the generator shown in FIG. 1.
Figure 14:
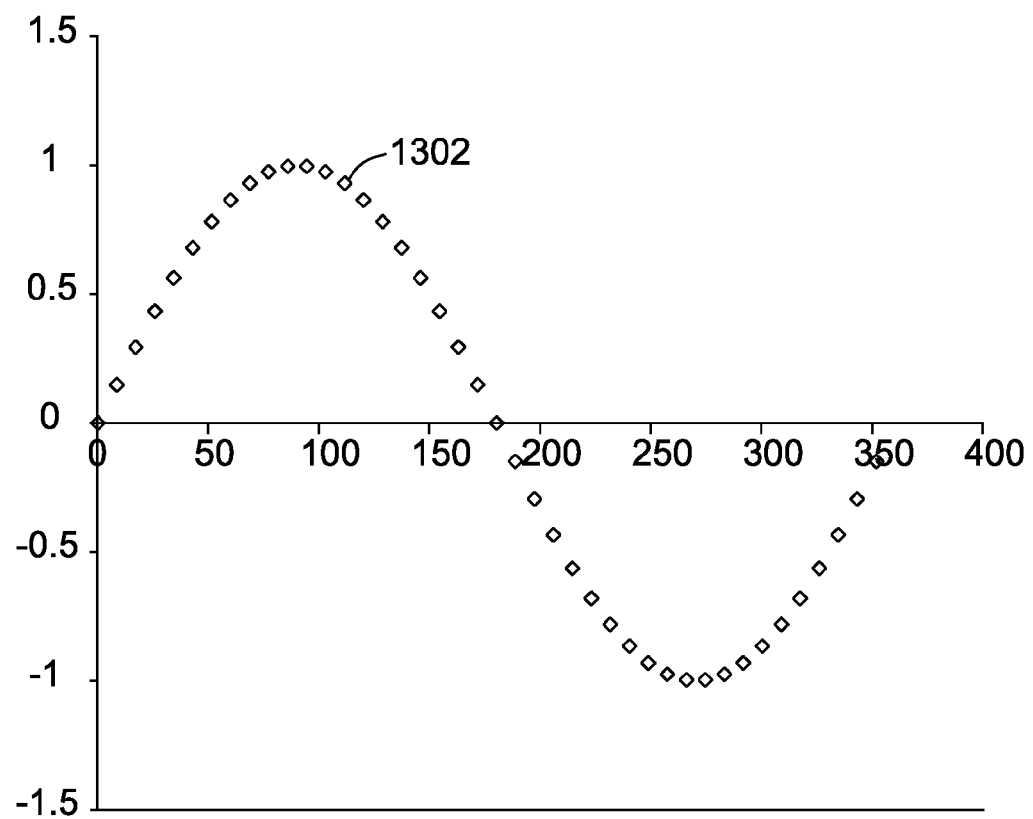
FIG. 14 is a graphical presentation of samples taken from the output signal waveform shown in FIG. 13 graphed as a function of the output signal phase.

This method for sampling the output signal will be further illustrated with reference to FIGS. 13 and 14. For this example, the output signal has a period of 2.1 microseconds (μs), corresponding to a frequency of 476.19048 kHz. The controller 128 samples the output signal at a rate of 1.5385 megasamples per second (MS/s), giving a sample period of 0.65 μs. Using equation (19), four is the smallest integer value that results in a sample shift greater than zero. Because n equals four, the sample shift is 0.5 μs. Plugging the sample shift into equation 3 results in a phase shift of about 85.7°. When S equals 42, equation (21) is satisfied. Thus, in this example, 42 samples will be acquired during a superperiod, which will include 14 output periods, and combined to represent one period of the output signal, with a resolution of 8.57°. FIG. 13 is a graphical representation of the output signal waveform 1300. The diamonds on the output signal waveform 1300 indicate samples 1302 of the output signal by controller 128. In FIG. 14, the samples 1302 are graphed as a function of the output signal phase of the samples 1302 producing a representation of a single period of the output signal waveform 1300. Each sample is spaced from its neighbor samples by 8.57° (the sampling resolution). This provides a much more accurate representation of a period of the output signal than would be provided by the three samples separated from each other by about 111° that are acquired during a single phase of the output signal.

Although described herein with reference to the output signal of the ablation generator 102, this sampling technique may be used to sample any suitable signal in any suitable apparatus. The signal to be sampled must have a fixed and known frequency. The signal needs to be substantially invariant, i.e., each period of the signal should be the same as each other period of the signal. The more invariant the signal, the more accurate the combined representation will be. The signal does not necessarily need to be invariant over multiple superperiods.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above without departing from the scope of the disclosure, it is intended that all matter contained in the above description and shown in the accompanying drawings shall be interpreted as illustrative and not in a limiting sense.

What is claimed is:

1. A multi-electrode ablation system comprising:
a power supply configured to be coupled to a plurality of electrodes; and
a controller coupled to the power supply, the controller configured to:
determine a thermal gain of each electrode of the plurality of electrodes, wherein the thermal gain of each electrode is determined based on temperature readings provided by one temperature sensor and wherein the thermal gain is a ratio of a change in measured temperature to an amount of applied power; and for each electrode of the plurality of electrodes, set a power limit based at least in part on said electrode's determined thermal gain, wherein the power limit establishes a maximum power that may be dissipated through said electrode, and wherein the power limit is proportional to a difference between the thermal gain and a threshold thermal gain.

2. The system set forth in claim 1 wherein the controller is configured to compare the determined thermal gain of each electrode to the threshold thermal gain.

3. The system set forth in claim 2 wherein the controller is configured to set the power limit at a predetermined power limit for each electrode for which the determined thermal gain equals or exceeds the threshold thermal gain.

4. The system set forth in claim 1 wherein the controller is configured, for each electrode, to set and maintain the power limit at a predetermined power limit until at least one startup condition for said electrode has been met.

5. The system set forth in claim 4 wherein the at least one startup condition is a temperature of said electrode reaching a predetermined temperature threshold.

6. The system set forth in claim 4 wherein the at least one startup condition is an energy dissipated through said electrode reaching a predetermined energy threshold.

7. The system set forth in claim 4 wherein the at least one startup condition is the first to occur of a temperature of said electrode reaching a predetermined temperature threshold and an energy dissipated through said electrode reaching a predetermined energy threshold.

8. A method of operating a multi-electrode ablation system, the method comprising:
determining a thermal gain of each electrode of a plurality of electrodes, wherein the thermal gain of each electrode is determined based on temperature readings provided by one temperature sensor and wherein the thermal gain is a ratio of a change in measured temperature to an amount of applied power; and
for each electrode of the plurality of electrodes, setting a power limit based at least in part on said electrode's determined thermal gain, wherein the power limit establishes a maximum power that may be dissipated through said electrode, and wherein the power limit is proportional to a difference between the thermal gain and a threshold thermal gain.

9. The method set forth in claim 8 further comprising comparing the determined thermal gain of each electrode to the threshold thermal gain.

10. The method set forth in claim 8 further comprising setting and maintaining the power limit at a predetermined power limit until at least one startup condition for said electrode has been met.

11. A multi-electrode ablation system comprising:
a power supply configured to be coupled to a plurality of electrodes; and
a controller coupled to the power supply, the controller configured to:
determine a thermal gain of each electrode of the plurality of electrodes, wherein the thermal gain of each electrode is determined based on temperature readings provided by one temperature sensor and wherein the thermal gain is a ratio of a change in measured temperature to an amount of applied power;
set a power limit for each electrode of the plurality of electrodes, wherein the power limit establishes a maximum power that may be dissipated through said electrode, and wherein the power limit is proportional to a difference between the thermal gain and a threshold thermal gain; and
for each electrode of the plurality of electrodes, determine whether or not to reduce the power limit for said electrode based at least in part on the determined thermal gain of said electrode.

12. The system set forth in claim 11 wherein the controller is further configured to compare the determined thermal gain for each electrode to the threshold thermal gain.

13. The system set forth in claim 12 wherein the controller is configured to determine not to reduce the power limit for an electrode when the determined thermal gain for said electrode is greater than or equal to the threshold thermal gain.

14. The system set forth in claim 12 wherein the controller is configured to determine to reduce the power limit for an electrode when the determined thermal gain for said electrode is less than the threshold thermal gain.

15. The system set forth in claim 11 wherein the controller is further configured to reduce the power limit for an electrode by an amount proportional to a difference value that is the difference between the determined thermal gain for said electrode and the threshold thermal gain when the determined thermal gain for said electrode is less than the threshold thermal gain.

16. The system set forth in claim 15 wherein the amount by which the power limit is reduced is determined by the product of a scaling factor and the difference value.

17. A method of operating a multi-electrode ablation system, the method comprising:
determining a thermal gain of each electrode of the plurality of electrodes, wherein the thermal gain of each electrode is determined based on temperature readings provided by one temperature sensor and wherein the thermal gain is a ratio of a change in measured temperature to an amount of applied power;
setting a power limit for each electrode of a plurality of electrodes, wherein the power limit establishes a maximum power that may be dissipated through said electrode, and wherein the power limit is proportional to a difference between the thermal gain and a threshold thermal gain; and
for each electrode of the plurality of electrodes, determining whether or not to reduce the power limit for said electrode based at least in part on the determined thermal gain of said electrode.

18. The method set forth in claim 17 further comprising comparing the determined thermal gain for each electrode to the threshold thermal gain.

19. The method set forth in claim 17 further comprising reducing the power limit for an electrode by an amount proportional to a difference value that is the difference between the determined thermal gain for said electrode and the threshold thermal gain when the determined thermal gain for said electrode is less than the threshold thermal gain.

20. The method set forth in claim 19 wherein the amount by which the power limit is reduced is determined by the product of a scaling factor and the difference value.

* * * * *